(12) United States Patent
Kumita et al.

(10) Patent No.: US 8,093,029 B2
(45) Date of Patent: Jan. 10, 2012

(54) BILIRUBIN OXIDASE MUTANT HAVING THERMAL STABILITY

(75) Inventors: Hideyuki Kumita, Kanagawa (JP); Yuichi Tokita, Kanagawa (JP); Yoshio Goto, Kanagawa (JP)

(73) Assignee: Sony Corporation, Tokyo (JP)

( * ) Notice: Subject to any disclaimer, the term of this patent is extended or adjusted under 35 U.S.C. 154(b) by 239 days.

(21) Appl. No.: 12/468,643

(22) Filed: May 19, 2009

(65) Prior Publication Data

US 2010/0129891 A1 May 27, 2010

Related U.S. Application Data

(63) Continuation-in-part of application No. 11/946,543, filed on Nov. 28, 2007, now abandoned.

(30) Foreign Application Priority Data

| Dec. 7, 2006 | (JP) | P2006-330352 |
| Jun. 19, 2007 | (JP) | P2007-160964 |

(51) Int. Cl.
| C12N 9/02 | (2006.01) |
| C12N 9/00 | (2006.01) |
| C12P 21/06 | (2006.01) |
| C12Q 1/00 | (2006.01) |
| C12Q 1/20 | (2006.01) |
| C07H 21/04 | (2006.01) |
| C07K 1/00 | (2006.01) |

(52) U.S. Cl. ........... 435/189; 435/183; 435/69.1; 435/4; 435/25; 536/23.2; 536/23.7; 536/23.74; 530/350

(58) Field of Classification Search ................ 435/189, 435/183, 69.1, 4, 25; 536/23.2, 23.7, 23.74; 530/350

See application file for complete search history.

(56) References Cited

U.S. PATENT DOCUMENTS

6,905,853 B1 * 6/2005 Wang ........................... 435/189

FOREIGN PATENT DOCUMENTS

| JP | 2000-083661 | 3/2000 |
| JP | 2004-071559 | 3/2004 |
| JP | 2004-089042 | 3/2004 |
| JP | 2004 089042 | * 3/2004 |
| JP | 2004-298185 | 10/2004 |
| JP | 2006-068003 | 3/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Kataoka et al., "Point Mutations at the Type I Cu Ligands, Cys457 and Met467, at the Putative Proton Donor, Asp105 in *Myrothecium verrucaria* Bilirubin and Reactions with Dioxygen," Biochemistry 2005, 44, 7004-7012.
Kataoka et al., "High-level expression of *Myrothecium verrucaria* bilirubin oxidase in *Pichia pastoris*, and its facile purification and characterization," Protein Expression & Purification, 41 (2005) 77-83.
Koikeda et al., "Molecular Cloing of the Gene for Bilirubin Oxidase From *Myrothecium verrucaria* and Its Expression in Yeast," Journal of Biological Chemistry, vol. 268, No. 25, pp. 18801-18809 (1993).
European Office Action issued on Jun. 30, 2008 for corresponding European Application EP07022903.
Kumita et al., "Improvement in the durability of Sony's biofuel cell," Prepr. Pap.-Am Chem. Soc., Div. Fuel Chem. 2009, 54 (2).
Sakai et al., "A high-power glucose/oxygen biofuel cell operating under quiscent conditions," ECS Transcations, 16 (38) 9-15 (2009).

* cited by examiner

Primary Examiner — Ganapathirama Raghu
(74) Attorney, Agent, or Firm — K&L Gates LLP

(57) ABSTRACT

A heat-resistant bilirubin oxidase mutant is disclosed. The bilirubin oxidase mutant is obtained by deletion, replacement, addition or insertion of at least one amino acid residue of a wild type amino sequence of SEQ. ID. No. 1 of a bilirubin oxidase derived from an imperfect filamentous fungus, *Myrothecium verrucaria*. A biocathode including a thermo stable bilirubin oxidase mutant immobilized thereon, and its use in a biofuel cell is disclosed.

1 Claim, 5 Drawing Sheets

FIG. 5

SEQUENCE LISTING

<160> NUMBER OF SEQ ID NOS: 67

<210> SEQ ID NO 1
<211> LENGTH: 534
<212> TYPE: PRT
<213> ORGANISM: Myrothecium verrucaria

<400> SEQUENCE: 1

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val

Asp Ala Leu Asn Leu Pro Ser Gly Tyr Gly Glu Phe Asp Ile Pro Met
            165                 170                 175

Ile Leu Thr Ser Lys Gln Tyr Thr Ala Asn Gly Asn Leu Val Thr Thr
        180                 185                 190

Asn Gly Glu Leu Asn Ser Phe Trp Gly Asp Val Ile His Val Asn Gly
    195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
        260                 265                 270

Met Ala Glu Arg Tyr Glu Val Val Phe Asp Phe Ser Asp Tyr Ala Gly
    275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
        340                 345                 350

Arg Phe Gly Arg Thr Gly Pro Thr Trp Thr Ile Asn Gly Val Ala Phe
    355                 360                 365

Ala Asp Val Gln Asn Arg Leu Leu Ala Asn Val Pro Val Gly Thr Val
370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
        420                 425                 430

Trp Leu Gly Arg Arg Glu Thr Val Val Val Glu Ala His Tyr Ala Pro
    435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
        500                 505                 510

Val Gln Ala Val Thr Glu Arg Ile Gln Thr Met Ala Glu Tyr Arg Pro
    515                 520                 525

Tyr Ala Ala Ala Asp Glu
        530

<210> SEQ ID NO 2
<211> LENGTH: 534
<212> TYPE: PRT
<213> ORGANISM: Artificial
<220> FEATURE:
<223> OTHER INFORMATION: Synthesized: Bilirubin oxidase mutant, abbreviated Q49K

<400> SEQUENCE: 2

```
Val Ala Gln Ile Ser Pro Gln Tyr Pro Met Phe Thr Val Pro Leu Pro
 1               5                  10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Lys Val Tyr Pro Asp Leu Gly Ser Ala Asp Leu Val Gly Tyr Asp Gly
50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
```

```
                      405                 410                 415
Asn Ala Arg Thr Val Met Pro Tyr Glu Ser Gly Leu Lys Asp Val Val
        420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
        450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
        500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 3
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Q72E

<400> SEQUENCE: 3

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Glu Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
```

```
                225                 230                 235                 240
Thr Asp Ala Ile Asp Thr Arg Leu Pro Phe Lys Val Ile Ala Ser Asp
                    245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 4
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V81L

<400> SEQUENCE: 4

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
```

-continued

```
            50                  55                  60
Met Ser Pro Gly Pro Thr Phe Gln Val Pro Arg Gly Val Glu Thr Val
 65                  70                  75                  80

Leu Arg Phe Ile Asn Asn Ala Glu Ala Pro Asn Ser Val His Leu His
                     85                  90                  95

Gly Ser Phe Ser Arg Ala Ala Phe Asp Gly Trp Ala Glu Asp Ile Thr
                    100                 105                 110

Glu Pro Gly Ser Phe Lys Asp Tyr Tyr Pro Asn Arg Gln Ser Ala
                115                 120                 125

Arg Thr Leu Trp Tyr His Asp His Ala Met His Ile Thr Ala Glu Asn
                130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                    165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                    245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                    325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                    405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
                450                 455                 460

His Asp Met Met Ala Ala Phe Asn Ala Thr Val Leu Pro Asp Tyr Gly
465                 470                 475                 480
```

```
Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 5
<211> LENGTH: 534
<212> TYPE: PRT
<213> ORGANISM: Artificial
<220> FEATURE:
<223> OTHER INFORMATION: Synthesized: Mutant bilirubin oxidase Y121S

<400> SEQUENCE: 5

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Ser Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
```

```
                305                 310                 315                 320
Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
            370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
                450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
                515                 520                 525

Tyr Ala Ala Ala Asp Glu
                530

<210> SEQ ID NO 6
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated R147P

<400> SEQUENCE: 6

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Tyr Pro Asn Arg Gln Ser Ala
            115                 120                 125

Arg Thr Leu Trp Tyr His Asp His Ala Met His Ile Thr Ala Glu Asn
```

-continued

```
            130                 135                 140
Ala Tyr Pro Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
                515                 520                 525

Tyr Ala Ala Ala Asp Glu
        530
```

<210> SEQ ID NO 7
<211> LENGTH: 534

-continued

<210> TYPE: PRT
<213> ORGANISM: Artificial
<220> FEATURE:
<223> OTHER INFORMATION: Synthesized: Bilirubin oxidase mutant, abbreviated A185S

<400> SEQUENCE: 7

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ser Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380
```

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
            405                 410                 415

Asn Ala Arg Thr Val Met Pro Tyr Glu Ser Gly Leu Lys Asp Val Val
        420                 425                 430

Trp Leu Gly Arg Arg Glu Thr Val Val Glu Ala His Tyr Ala Pro
    435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 8
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated P210L

<400> SEQUENCE: 8

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Gly Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

```
Gln Leu Trp Pro Phe Lys Asn Val Glu Pro Arg Lys Tyr Arg Phe Arg
    210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
    290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Val Gly Thr Val
    370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Glu Ala His Tyr Ala Pro
        435                 440                 445
Phe Pro Gly Val Tyr Met Phe His Cys His Asn Leu Ile His Glu Asp
    450                 455                 460
His Asp Met Met Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
        515                 520                 525
Tyr Ala Ala Ala Asp Glu
    530

<210> SEQ ID NO 9
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated F225V

<400> SEQUENCE: 9

Val Ala Gln Ile Ser Pro Gln Tyr Pro Met Phe Thr Val Pro Leu Pro
1               5                   10                  15
Ile Pro Pro Val Lys Gln Pro Arg Leu Thr Val Thr Asn Pro Val Asn
            20                  25                  30
```

```
Gly Gln Glu Ile Trp Tyr Tyr Glu Val Glu Ile Lys Pro Phe Thr His
    35                  40                  45
Gln Val Tyr Pro Asp Leu Gly Ser Ala Asp Leu Val Gly Tyr Asp Gly
50                  55                  60
Met Ser Pro Gly Pro Thr Phe Gln Val Pro Arg Gly Val Glu Thr Val
65                  70                  75                  80
Val Arg Phe Ile Asn Asn Ala Glu Ala Pro Asn Ser Val His Leu His
                85                  90                  95
Gly Ser Phe Ser Arg Ala Ala Phe Asp Gly Trp Ala Glu Asp Ile Thr
                100                 105                 110
Glu Pro Gly Ser Phe Lys Asp Tyr Tyr Pro Asn Arg Gln Ser Ala
            115                 120                 125
Arg Thr Leu Trp Tyr His Asp His Ala Met His Ile Thr Ala Glu Asn
        130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
                180                 185                 190
Asn Gly Glu Leu Asn Ser Phe Trp Gly Asp Val Ile His Val Asn Gly
            195                 200                 205
Gln Pro Trp Pro Phe Lys Asn Val Glu Pro Arg Lys Tyr Arg Phe Arg
    210                 215                 220
Val Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
    275                 280                 285
Lys Thr Ile Glu Leu Arg Asn Leu Gly Gly Ser Ile Gly Gly Ile Gly
290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Val Gly Thr Val
370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Glu Ala His Tyr Ala Pro
        435                 440                 445
Phe Pro Gly Val Tyr Met Phe His Cys His Asn Leu Ile His Glu Asp
450                 455                 460
```

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Gly Tyr Arg Pro
        515                 520                 525

Tyr Ala Ala Ala Asp Glu
        530

<210> SEQ ID NO 10
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated G258V

<400> SEQUENCE: 10

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Val Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

```
Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 11
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V

<400> SEQUENCE: 11

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110
```

```
Glu Pro Gly Ser Phe Lys Asp Tyr Tyr Pro Asn Arg Gln Ser Ala
            115                 120                 125
Arg Thr Leu Trp Tyr His Asp His Ala Met His Ile Thr Ala Glu Asn
130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
            195                 200                 205
Gln Pro Trp Pro Phe Lys Asn Val Glu Pro Arg Lys Tyr Arg Phe Arg
210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Val Asp Thr Ser Leu Leu Tyr Ile Ser
            260                 265                 270
Met Ala Glu Arg Tyr Glu Val Val Phe Asp Phe Ser Asp Tyr Ala Gly
            275                 280                 285
Lys Thr Ile Glu Leu Arg Asn Leu Gly Gly Ser Ile Gly Gly Ile Gly
            290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
            355                 360                 365
Ala Asp Val Gln Asn Arg Leu Leu Ala Asn Val Pro Val Gly Thr Val
            370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Val Glu Ala His Tyr Ala Pro
            435                 440                 445
Phe Pro Gly Val Tyr Met Phe His Cys His Asn Leu Ile His Glu Asp
            450                 455                 460
His Asp Met Met Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
            515                 520                 525
Tyr Ala Ala Ala Asp Glu
```

<210> SEQ ID NO 12
<211> LENGTH: 534
<212> TYPE: PRT
<213> ORGANISM: Artificial
<220> FEATURE:
<223> OTHER INFORMATION: Synthesized: Bilirubin oxidase mutant, abbreviated D322N

<400> SEQUENCE: 12

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asn Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
```

```
                355                 360                 365
Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 13
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated N335S

<400> SEQUENCE: 13

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65              70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
```

180                 185                 190
Asn Gly Glu Leu Asn Ser Phe Trp Gly Asp Val Ile His Val Asn Gly
            195                 200                 205

Gln Pro Trp Pro Phe Lys Asn Val Glu Pro Arg Lys Tyr Arg Phe Arg
        210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Ser Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 14
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated R356L

<400> SEQUENCE: 14

Val Ala Gln Ile Ser Pro Gln Tyr Pro Met Phe Thr Val Pro Leu Pro

-continued

```
1               5                   10                  15
Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
                35                  40                  45

Gln Val Tyr Pro Asp Leu Gly Ser Ala Asp Leu Val Gly Tyr Asp Gly
 50                  55                  60

Met Ser Pro Gly Pro Thr Phe Gln Val Pro Arg Gly Val Glu Thr Val
 65                  70                  75                  80

Val Arg Phe Ile Asn Asn Ala Glu Ala Pro Asn Ser Val His Leu His
                 85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Pro Asn Arg Gln Ser Ala
                115                 120                 125

Arg Thr Leu Trp Tyr His Asp His Ala Met His Ile Thr Ala Glu Asn
                130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Leu Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430
```

```
Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Gly Tyr Arg Pro
        515                 520                 525

Tyr Ala Ala Ala Asp Glu
    530

<210> SEQ ID NO 15
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated P359S

<400> SEQUENCE: 15

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255
```

-continued

```
Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Ser Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 16
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated D370Y

<400> SEQUENCE: 16

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80
```

-continued

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Tyr Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

```
Val Gln Ala Val Thr Glu Arg Ile Gln Thr Met Ala Glu Tyr Arg Pro
        515                 520                 525
Tyr Ala Ala Ala Asp Glu
        530

<210> SEQ ID NO 17
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V371A

<400> SEQUENCE: 17

Val Ala Gln Ile Ser Pro Gln Tyr Pro Met Phe Thr Val Pro Leu Pro
1               5                   10                  15
Ile Pro Pro Val Lys Gln Pro Arg Leu Thr Val Thr Asn Pro Val Asn
                20                  25                  30
Gly Gln Glu Ile Trp Tyr Tyr Glu Val Glu Ile Lys Pro Phe Thr His
            35                  40                  45
Gln Val Tyr Pro Asp Leu Gly Ser Ala Asp Leu Val Gly Tyr Asp Gly
        50                  55                  60
Met Ser Pro Gly Pro Thr Phe Gln Val Pro Arg Gly Val Glu Thr Val
65                  70                  75                  80
Val Arg Phe Ile Asn Asn Ala Glu Ala Pro Asn Ser Val His Leu His
                85                  90                  95
Gly Ser Phe Ser Arg Ala Ala Phe Asp Gly Trp Ala Glu Asp Ile Thr
            100                 105                 110
Glu Pro Gly Ser Phe Lys Asp Tyr Tyr Pro Asn Arg Gln Ser Ala
        115                 120                 125
Arg Thr Leu Trp Tyr His Asp His Ala Met His Ile Thr Ala Glu Asn
130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
        195                 200                 205
Gln Pro Trp Pro Phe Lys Asn Val Glu Pro Arg Lys Tyr Arg Phe Arg
    210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
    290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
```

-continued

Arg Asp Val Pro Phe Pro Ser Pro Thr Thr Asn Thr Pro Arg Gln Phe
              340                 345                 350

Arg Phe Gly Arg Thr Gly Pro Thr Trp Thr Ile Asn Gly Val Ala Phe
          355                 360                 365

Ala Asp Ala Gln Asn Arg Leu Leu Ala Asn Val Pro Val Gly Thr Val
      370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
              405                 410                 415

Asn Ala Arg Thr Val Met Pro Tyr Glu Ser Gly Leu Lys Asp Val Val
          420                 425                 430

Trp Leu Gly Arg Arg Glu Thr Val Val Glu Ala His Tyr Ala Pro
          435                 440                 445

Phe Pro Gly Val Tyr Met Phe His Cys His Asn Leu Ile His Glu Asp
      450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
              485                 490                 495

Arg Pro Tyr Glu Leu Gly Glu Phe Gln Ala Gln Ser Gly Gln Phe Ser
          500                 505                 510

Val Gln Ala Val Thr Glu Arg Ile Gln Thr Met Ala Glu Tyr Arg Pro
      515                 520                 525

Tyr Ala Ala Ala Asp Glu
      530

<210> SEQ ID NO 18
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated P423L

<400> SEQUENCE: 18

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
              85                  90                  95

Gly Ser Phe Ser Arg Ala Ala Phe Asp Gly Trp Ala Glu Asp Ile Thr
          100                 105                 110

Glu Pro Gly Ser Phe Lys Asp Tyr Tyr Pro Asn Arg Gln Ser Ala
      115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

-continued

```
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
        195                 200                 205
Gln Pro Trp Pro Phe Lys Asn Val Glu Pro Arg Lys Tyr Arg Phe Arg
    210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
    290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Val Gly Thr Val
    370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Leu Tyr Glu Ser Gly Leu Lys Asp Val Val
            420                 425                 430
Trp Leu Gly Arg Arg Glu Thr Val Val Glu Ala His Tyr Ala Pro
        435                 440                 445
Phe Pro Gly Val Tyr Met Phe His Cys His Asn Leu Ile His Glu Asp
    450                 455                 460
His Asp Met Met Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
        515                 520                 525
Tyr Ala Ala Ala Asp Glu
    530
```

<210> SEQ ID NO 19
<211> LENGTH: 534
<212> TYPE: PRT
<213> ORGANISM: Artificial
<220> FEATURE:
<223> OTHER INFORMATION: Synthesized: Bilirubin oxidase mutant, abbreviated M468V

<400> SEQUENCE: 19

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
```

```
                        405                 410                 415
Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
            450                 455                 460

His Asp Met Val Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
            485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 20
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated L476P

<400> SEQUENCE: 20

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
```

-continued

```
                225                 230                 235                 240
Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 21
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V513L

<400> SEQUENCE: 21

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
```

```
              50                  55                  60
Met Ser Pro Gly Pro Thr Phe Gln Val Pro Arg Gly Val Glu Thr Val
 65                  70                  75                  80

Val Arg Phe Ile Asn Asn Ala Glu Ala Pro Asn Ser Val His Leu His
                     85                  90                  95

Gly Ser Phe Ser Arg Ala Ala Phe Asp Gly Trp Ala Glu Asp Ile Thr
                    100                 105                 110

Glu Pro Gly Ser Phe Lys Asp Tyr Tyr Pro Asn Arg Gln Ser Ala
                115                 120                 125

Arg Thr Leu Trp Tyr His Asp His Ala Met His Ile Thr Ala Glu Asn
                130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                    165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                    245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                    325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                    405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
                450                 455                 460

His Asp Met Met Ala Ala Phe Asn Ala Thr Val Leu Pro Asp Tyr Gly
465                 470                 475                 480
```

```
Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Leu Gln Ala Val Thr Glu Arg Ile Gln Thr Met Ala Glu Tyr Arg Pro
        515                 520                 525

Tyr Ala Ala Ala Asp Glu
        530

<210> SEQ ID NO 22
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Q49K/V371A

<400> SEQUENCE: 22

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Lys Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300
```

```
Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
            325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
            355                 360                 365

Ala Asp Ala Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
    530

<210> SEQ ID NO 23
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Q72E/P210L

<400> SEQUENCE: 23

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Glu Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125
```

```
Arg Thr Leu Trp Tyr His Asp His Ala Met His Ile Thr Ala Glu Asn
    130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
        195                 200                 205
Gln Leu Trp Pro Phe Lys Asn Val Glu Pro Arg Lys Tyr Arg Phe Arg
    210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
    290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Val Gly Thr Val
    370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Glu Ala His Tyr Ala Pro
        435                 440                 445
Phe Pro Gly Val Tyr Met Phe His Cys His Asn Leu Ile His Glu Asp
450                 455                 460
His Asp Met Met Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
        515                 520                 525
Tyr Ala Ala Ala Asp Glu
    530

<210> SEQ ID NO 24
```

<211> LENGTH: 534
<212> TYPE: PRT
<213> ORGANISM: Artificial
<220> FEATURE:
<223> OTHER INFORMATION: Synthesized: Bilirubin oxidase mutant, abbreviated Q72E/A264V

<400> SEQUENCE: 24

| Val | Ala | Gln | Ile | Ser | Pro | Gln | Tyr | Pro | Met | Phe | Thr | Val | Pro | Leu | Pro |
|-----|-----|-----|-----|-----|-----|-----|-----|-----|-----|-----|-----|-----|-----|-----|-----|
| 1 | | | | 5 | | | | | 10 | | | | | 15 | |

| Ile | Pro | Pro | Val | Lys | Gln | Pro | Arg | Leu | Thr | Val | Thr | Asn | Pro | Val | Asn |
| | | | 20 | | | | | 25 | | | | | 30 | | |

| Gly | Gln | Glu | Ile | Trp | Tyr | Tyr | Glu | Val | Glu | Ile | Lys | Pro | Phe | Thr | His |
| | | | 35 | | | | 40 | | | | | 45 | | | |

| Gln | Val | Tyr | Pro | Asp | Leu | Gly | Ser | Ala | Asp | Leu | Val | Gly | Tyr | Asp | Gly |
| | 50 | | | | | 55 | | | | | 60 | | | | |

| Met | Ser | Pro | Gly | Pro | Thr | Phe | Glu | Val | Pro | Arg | Gly | Val | Glu | Thr | Val |
| 65 | | | | | 70 | | | | 75 | | | | | 80 | |

| Val | Arg | Phe | Ile | Asn | Asn | Ala | Glu | Ala | Pro | Asn | Ser | Val | His | Leu | His |
| | | | | 85 | | | | 90 | | | | | 95 | | |

| Gly | Ser | Phe | Ser | Arg | Ala | Ala | Phe | Asp | Gly | Trp | Ala | Glu | Asp | Ile | Thr |
| | | | 100 | | | | | 105 | | | | | 110 | | |

| Glu | Pro | Gly | Ser | Phe | Lys | Asp | Tyr | Tyr | Tyr | Pro | Asn | Arg | Gln | Ser | Ala |
| | | 115 | | | | | 120 | | | | | 125 | | | |

| Arg | Thr | Leu | Trp | Tyr | His | Asp | His | Ala | Met | His | Ile | Thr | Ala | Glu | Asn |
| | 130 | | | | | 135 | | | | | 140 | | | | |

| Ala | Tyr | Arg | Gly | Gln | Ala | Gly | Leu | Tyr | Met | Leu | Thr | Asp | Pro | Ala | Glu |
| 145 | | | | | 150 | | | | | 155 | | | | | 160 |

| Asp | Ala | Leu | Asn | Leu | Pro | Ser | Gly | Tyr | Gly | Glu | Phe | Asp | Ile | Pro | Met |
| | | | | 165 | | | | | 170 | | | | | 175 | |

| Ile | Leu | Thr | Ser | Lys | Gln | Tyr | Thr | Ala | Asn | Gly | Asn | Leu | Val | Thr | Thr |
| | | | 180 | | | | | 185 | | | | | 190 | | |

| Asn | Gly | Glu | Leu | Asn | Ser | Phe | Trp | Gly | Asp | Val | Ile | His | Val | Asn | Gly |
| | | 195 | | | | | 200 | | | | | 205 | | | |

| Gln | Pro | Trp | Pro | Phe | Lys | Asn | Val | Glu | Pro | Arg | Lys | Tyr | Arg | Phe | Arg |
| | 210 | | | | | 215 | | | | | 220 | | | | |

| Phe | Leu | Asp | Ala | Ala | Val | Ser | Arg | Ser | Phe | Gly | Leu | Tyr | Phe | Ala | Asp |
| 225 | | | | | 230 | | | | | 235 | | | | | 240 |

| Thr | Asp | Ala | Ile | Asp | Thr | Arg | Leu | Pro | Phe | Lys | Val | Ile | Ala | Ser | Asp |
| | | | | 245 | | | | | 250 | | | | | 255 | |

| Ser | Gly | Leu | Leu | Glu | His | Pro | Val | Asp | Thr | Ser | Leu | Leu | Tyr | Ile | Ser |
| | | | 260 | | | | | 265 | | | | | 270 | | |

| Met | Ala | Glu | Arg | Tyr | Glu | Val | Val | Phe | Asp | Phe | Ser | Asp | Tyr | Ala | Gly |
| | | 275 | | | | | 280 | | | | | 285 | | | |

| Lys | Thr | Ile | Glu | Leu | Arg | Asn | Leu | Gly | Gly | Ser | Ile | Gly | Gly | Ile | Gly |
| | 290 | | | | | 295 | | | | | 300 | | | | |

| Thr | Asp | Thr | Asp | Tyr | Asp | Asn | Thr | Asp | Lys | Val | Met | Arg | Phe | Val | Val |
| 305 | | | | | 310 | | | | | 315 | | | | | 320 |

| Ala | Asp | Asp | Thr | Thr | Gln | Pro | Asp | Thr | Ser | Val | Val | Pro | Ala | Asn | Leu |
| | | | | 325 | | | | | 330 | | | | | 335 | |

| Arg | Asp | Val | Pro | Phe | Pro | Ser | Pro | Thr | Thr | Asn | Thr | Pro | Arg | Gln | Phe |
| | | | 340 | | | | | 345 | | | | | 350 | | |

| Arg | Phe | Gly | Arg | Thr | Gly | Pro | Thr | Trp | Thr | Ile | Asn | Gly | Val | Ala | Phe |
| | | 355 | | | | | 360 | | | | | 365 | | | |

| Ala | Asp | Val | Gln | Asn | Arg | Leu | Leu | Ala | Asn | Val | Pro | Val | Gly | Thr | Val |
| | 370 | | | | | 375 | | | | | 380 | | | | |

```
Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
            405                 410                 415

Asn Ala Arg Thr Val Met Pro Tyr Glu Ser Gly Leu Lys Asp Val Val
        420                 425                 430

Trp Leu Gly Arg Arg Glu Thr Val Val Glu Ala His Tyr Ala Pro
    435                 440                 445

Phe Pro Gly Val Tyr Met Phe His Cys His Asn Leu Ile His Glu Asp
        450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530
```

<210> SEQ ID NO 25
<211> LENGTH: 534
<212> TYPE: PRT
<213> ORGANISM: Artificial
<220> FEATURE:
<223> OTHER INFORMATION: Synthesized: Bilirubin oxidase mutant, abbreviated V81L/R147P

<400> SEQUENCE: 25

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Leu Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Pro Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205
```

```
Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 26
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V81L/P423L

<400> SEQUENCE: 26

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30
```

```
Gly Gln Glu Ile Trp Tyr Tyr Glu Val Glu Ile Lys Pro Phe Thr His
             35                  40                  45
Gln Val Tyr Pro Asp Leu Gly Ser Ala Asp Leu Val Gly Tyr Asp Gly
 50                  55                  60
Met Ser Pro Gly Pro Thr Phe Gln Val Pro Arg Gly Val Glu Thr Val
 65                  70                  75                  80
Leu Arg Phe Ile Asn Asn Ala Glu Ala Pro Asn Ser Val His Leu His
             85                  90                  95
Gly Ser Phe Ser Arg Ala Ala Phe Asp Gly Trp Ala Glu Asp Ile Thr
            100                 105                 110
Glu Pro Gly Ser Phe Lys Asp Tyr Tyr Tyr Pro Asn Arg Gln Ser Ala
            115                 120                 125
Arg Thr Leu Trp Tyr His Asp His Ala Met His Ile Thr Ala Glu Asn
            130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
                180                 185                 190
Asn Gly Glu Leu Asn Ser Phe Trp Gly Asp Val Ile His Val Asn Gly
            195                 200                 205
Gln Pro Trp Pro Phe Lys Asn Val Glu Pro Arg Lys Tyr Arg Phe Arg
            210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
                260                 265                 270
Met Ala Glu Arg Tyr Glu Val Val Phe Asp Phe Ser Asp Tyr Ala Gly
            275                 280                 285
Lys Thr Ile Glu Leu Arg Asn Leu Gly Gly Ser Ile Gly Gly Ile Gly
            290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
            355                 360                 365
Ala Asp Val Gln Asn Arg Leu Leu Ala Asn Val Pro Val Gly Thr Val
            370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Leu Tyr Glu Ser Gly Leu Lys Asp Val Val
            420                 425                 430
Trp Leu Gly Arg Arg Glu Thr Val Val Glu Ala His Tyr Ala Pro
            435                 440                 445
Phe Pro Gly Val Tyr Met Phe His Cys His Asn Leu Ile His Glu Asp
```

```
                    450                 455                 460
His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Gly Tyr Arg Pro
        515                 520                 525

Tyr Ala Ala Asp Glu
    530

<210> SEQ ID NO 27
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Y121S/L476P

<400> SEQUENCE: 27

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Ser Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
```

```
                275                 280                 285
Lys Thr Ile Glu Leu Arg Asn Leu Gly Gly Ser Ile Gly Gly Ile Gly
            290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Gly Tyr Arg Pro
        515                 520                 525

Tyr Ala Ala Ala Asp Glu
    530

<210> SEQ ID NO 28
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A185S/G258V

<400> SEQUENCE: 28

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
```

```
                    100             105             110
Glu Pro Gly Ser Phe Lys Asp Tyr Tyr Pro Asn Arg Gln Ser Ala
            115             120             125

Arg Thr Leu Trp Tyr His Asp His Ala Met His Ile Thr Ala Glu Asn
130             135             140

Ala Tyr Arg Gly Gln Ala Gly Leu Tyr Met Leu Thr Asp Pro Ala Glu
145             150             155             160

Asp Ala Leu Asn Leu Pro Ser Gly Tyr Gly Glu Phe Asp Ile Pro Met
                165             170             175

Ile Leu Thr Ser Lys Gln Tyr Thr Ser Asn Gly Asn Leu Val Thr Thr
            180             185             190

Asn Gly Glu Leu Asn Ser Phe Trp Gly Asp Val Ile His Val Asn Gly
            195             200             205

Gln Pro Trp Pro Phe Lys Asn Val Glu Pro Arg Lys Tyr Arg Phe Arg
210             215             220

Phe Leu Asp Ala Ala Val Ser Arg Ser Phe Gly Leu Tyr Phe Ala Asp
225             230             235             240

Thr Asp Ala Ile Asp Thr Arg Leu Pro Phe Lys Val Ile Ala Ser Asp
                245             250             255

Ser Val Leu Leu Glu His Pro Ala Asp Thr Ser Leu Leu Tyr Ile Ser
            260             265             270

Met Ala Glu Arg Tyr Glu Val Val Phe Asp Phe Ser Asp Tyr Ala Gly
            275             280             285

Lys Thr Ile Glu Leu Arg Asn Leu Gly Gly Ser Ile Gly Gly Ile Gly
            290             295             300

Thr Asp Thr Asp Tyr Asp Asn Thr Asp Lys Val Met Arg Phe Val Val
305             310             315             320

Ala Asp Asp Thr Thr Gln Pro Asp Thr Ser Val Val Pro Ala Asn Leu
                325             330             335

Arg Asp Val Pro Phe Pro Ser Pro Thr Thr Asn Thr Pro Arg Gln Phe
            340             345             350

Arg Phe Gly Arg Thr Gly Pro Thr Trp Thr Ile Asn Gly Val Ala Phe
            355             360             365

Ala Asp Val Gln Asn Arg Leu Leu Ala Asn Val Pro Val Gly Thr Val
            370             375             380

Glu Arg Trp Glu Leu Ile Asn Ala Gly Asn Gly Trp Thr His Pro Ile
385             390             395             400

His Ile His Leu Val Asp Phe Lys Val Ile Ser Arg Thr Ser Gly Asn
                405             410             415

Asn Ala Arg Thr Val Met Pro Tyr Glu Ser Gly Leu Lys Asp Val Val
            420             425             430

Trp Leu Gly Arg Arg Glu Thr Val Val Glu Ala His Tyr Ala Pro
            435             440             445

Phe Pro Gly Val Tyr Met Phe His Cys His Asn Leu Ile His Glu Asp
            450             455             460

His Asp Met Met Ala Ala Phe Asn Ala Thr Val Leu Pro Asp Tyr Gly
465             470             475             480

Tyr Asn Ala Thr Val Phe Val Asp Pro Met Glu Glu Leu Trp Gln Ala
                485             490             495

Arg Pro Tyr Glu Leu Gly Glu Phe Gln Ala Gln Ser Gly Gln Phe Ser
            500             505             510

Val Gln Ala Val Thr Glu Arg Ile Gln Thr Met Ala Glu Tyr Arg Pro
            515             520             525
```

Tyr Ala Ala Ala Asp Glu
    530

<210> SEQ ID NO 29
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated P210L/A264V

<400> SEQUENCE: 29

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Leu Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

```
Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
        450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
            515                 520                 525

Tyr Ala Ala Ala Asp Glu
        530

<210> SEQ ID NO 30
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated F225V/D322N

<400> SEQUENCE: 30

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175
```

```
Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
            195                 200                 205

Gln Pro Trp Pro Phe Lys Asn Val Glu Pro Arg Lys Tyr Arg Phe Arg
210                 215                 220

Val Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
            245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
            275                 280                 285

Lys Thr Ile Glu Leu Arg Asn Leu Gly Gly Ser Ile Gly Gly Ile Gly
            290                 295                 300

Thr Asp Thr Asp Tyr Asp Asn Thr Asp Lys Val Met Arg Phe Val Val
305                 310                 315                 320

Ala Asn Asp Thr Thr Gln Pro Asp Thr Ser Val Val Pro Ala Asn Leu
            325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
            355                 360                 365

Ala Asp Val Gln Asn Arg Leu Leu Ala Asn Val Pro Val Gly Thr Val
            370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
            405                 410                 415

Asn Ala Arg Thr Val Met Pro Tyr Glu Ser Gly Leu Lys Asp Val Val
            420                 425                 430

Trp Leu Gly Arg Arg Glu Thr Val Val Val Glu Ala His Tyr Ala Pro
            435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
            485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 31
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated F225V/L476P

<400> SEQUENCE: 31
```

```
Val Ala Gln Ile Ser Pro Gln Tyr Pro Met Phe Thr Val Pro Leu Pro
 1               5                  10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Tyr Pro Asn Arg Gln Ser Ala
                115                 120                 125

Arg Thr Leu Trp Tyr His Asp His Ala Met His Ile Thr Ala Glu Asn
        130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
210                 215                 220

Val Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
        370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430
```

```
Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 32
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V/R356L

<400> SEQUENCE: 32

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Gly Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255
```

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Leu Thr Gly Pro Thr Trp Thr Ile Asn Gly Val Ala Phe
            355                 360                 365

Ala Asp Val Gln Asn Arg Leu Leu Ala Asn Val Pro Val Gly Thr Val
        370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
            515                 520                 525

Tyr Ala Ala Ala Asp Glu
    530

<210> SEQ ID NO 33
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V/L476P

<400> SEQUENCE: 33

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

```
Val Arg Phe Ile Asn Asn Ala Glu Ala Pro Asn Ser Val His Leu His
                85                  90                  95
Gly Ser Phe Ser Arg Ala Ala Phe Asp Gly Trp Ala Glu Asp Ile Thr
            100                 105                 110
Glu Pro Gly Ser Phe Lys Asp Tyr Tyr Pro Asn Arg Gln Ser Ala
        115                 120                 125
Arg Thr Leu Trp Tyr His Asp His Ala Met His Ile Thr Ala Glu Asn
    130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
        195                 200                 205
Gln Pro Trp Pro Phe Lys Asn Val Glu Pro Arg Lys Tyr Arg Phe Arg
    210                 215                 220
Phe Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Val Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
    290                 295                 300
Thr Asp Thr Asp Tyr Asp Asn Thr Asp Lys Val Met Arg Phe Val Val
305                 310                 315                 320
Ala Asp Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Val Gly Thr Val
    370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Glu Ala His Tyr Ala Pro
        435                 440                 445
Phe Pro Gly Val Tyr Met Phe His Cys His Asn Leu Ile His Glu Asp
    450                 455                 460
His Asp Met Met Ala Ala Phe Asn Ala Thr Val Pro Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
```

```
                    500                 505                 510
Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 34
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated D322N/M468V

<400> SEQUENCE: 34

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asn Asp Thr Thr Gln Pro Asp Thr Ser Val Val Pro Ala Asn Leu
```

```
                    325                 330                 335
Arg Asp Val Pro Phe Pro Ser Pro Thr Thr Asn Thr Pro Arg Gln Phe
                340                 345                 350
Arg Phe Gly Arg Thr Gly Pro Thr Trp Thr Ile Asn Gly Val Ala Phe
                355                 360                 365
Ala Asp Val Gln Asn Arg Leu Leu Ala Asn Val Pro Val Gly Thr Val
            370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
                420                 425                 430
Trp Leu Gly Arg Arg Glu Thr Val Val Glu Ala His Tyr Ala Pro
            435                 440                 445
Phe Pro Gly Val Tyr Met Phe His Cys His Asn Leu Ile His Glu Asp
            450                 455                 460
His Asp Met Val Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
            515                 520                 525
Tyr Ala Ala Ala Asp Glu
            530

<210> SEQ ID NO 35
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated N335S/P423L

<400> SEQUENCE: 35

Val Ala Gln Ile Ser Pro Gln Tyr Pro Met Phe Thr Val Pro Leu Pro
1               5                   10                  15
Ile Pro Pro Val Lys Gln Pro Arg Leu Thr Val Thr Asn Pro Val Asn
                20                  25                  30
Gly Gln Glu Ile Trp Tyr Tyr Glu Val Glu Ile Lys Pro Phe Thr His
            35                  40                  45
Gln Val Tyr Pro Asp Leu Gly Ser Ala Asp Leu Val Gly Tyr Asp Gly
        50                  55                  60
Met Ser Pro Gly Pro Thr Phe Gln Val Pro Arg Gly Val Glu Thr Val
65                  70                  75                  80
Val Arg Phe Ile Asn Asn Ala Glu Ala Pro Asn Ser Val His Leu His
                85                  90                  95
Gly Ser Phe Ser Arg Ala Ala Phe Asp Gly Trp Ala Glu Asp Ile Thr
                100                 105                 110
Glu Pro Gly Ser Phe Lys Asp Tyr Tyr Pro Asn Arg Gln Ser Ala
            115                 120                 125
Arg Thr Leu Trp Tyr His Asp His Ala Met His Ile Thr Ala Glu Asn
            130                 135                 140
Ala Tyr Arg Gly Gln Ala Gly Leu Tyr Met Leu Thr Asp Pro Ala Glu
```

```
            145                 150                 155                 160
Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Ser Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Leu Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 36
<211> LENGTH: 534
<212> TYPE: PRT
<213> ORGANISM: Artificial
<220> FEATURE:
```

<223> OTHER INFORMATION: Synthesized: Bilirubin oxidase mutant, abbreviated R356L/L476P

<400> SEQUENCE: 36

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65              70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Leu Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400
```

```
His Ile His Leu Val Asp Phe Lys Val Ile Ser Arg Thr Ser Gly Asn
            405                 410                 415

Asn Ala Arg Thr Val Met Pro Tyr Glu Ser Gly Leu Lys Asp Val Val
        420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 37
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V371A/V513L

<400> SEQUENCE: 37

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220
```

```
Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
            245                 250                 255

Ser Gly Leu Leu Glu His Pro Ala Asp Thr Ser Leu Leu Tyr Ile Ser
        260                 265                 270

Met Ala Glu Arg Tyr Glu Val Val Phe Asp Phe Ser Asp Tyr Ala Gly
    275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Ala Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Leu Gln Ala Val Thr Glu Arg Ile Gln Thr Met Ala Glu Tyr Arg Pro
        515                 520                 525

Tyr Ala Ala Ala Asp Glu
    530

<210> SEQ ID NO 38
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Q49K/V371A/V513L

<400> SEQUENCE: 38

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45
```

-continued

```
Lys Val Tyr Pro Asp Leu Gly Ser Ala Asp Leu Val Gly Tyr Asp Gly
 50                  55                  60

Met Ser Pro Gly Pro Thr Phe Gln Val Pro Arg Gly Val Glu Thr Val
 65                  70                  75                  80

Val Arg Phe Ile Asn Asn Ala Glu Ala Pro Asn Ser Val His Leu His
                 85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Tyr Pro Asn Arg Gln Ser Ala
            115                 120                 125

Arg Thr Leu Trp Tyr His Asp His Ala Met His Ile Thr Ala Glu Asn
        130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Ala Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480
```

```
Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Leu Gln Ala Val Thr Glu Arg Ile Gln Thr Met Ala Glu Tyr Arg Pro
        515                 520                 525

Tyr Ala Ala Ala Asp Glu
    530

<210> SEQ ID NO 39
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Q72E/P210L/A264V

<400> SEQUENCE: 39

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Glu Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Leu Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300
```

```
Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
            325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
            355                 360                 365

Ala Asp Val Gln Asn Arg Leu Leu Ala Asn Val Pro Val Gly Thr Val
            370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
            405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
            450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
            485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 40
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V81L/N335S/P423L

<400> SEQUENCE: 40

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Leu Arg Phe Ile Asn Asn Ala Glu Ala Pro Asn Ser Val His Leu His
            85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
            115                 120                 125
```

Arg Thr Leu Trp Tyr His Asp His Ala Met His Ile Thr Ala Glu Asn
            130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
            195                 200                 205

Gln Pro Trp Pro Phe Lys Asn Val Glu Pro Arg Lys Tyr Arg Phe Arg
            210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
            275                 280                 285

Lys Thr Ile Glu Leu Arg Asn Leu Gly Gly Ser Ile Gly Gly Ile Gly
            290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Ser Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
            355                 360                 365

Ala Asp Val Gln Asn Arg Leu Leu Ala Asn Val Pro Val Gly Thr Val
            370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Leu Tyr Glu Ser Gly Leu Lys Asp Val Val
                420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
            450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 41
<211> LENGTH: 534
<212> TYPE: PRT
<213> ORGANISM: Artificial
<220> FEATURE:
<223> OTHER INFORMATION: Synthesized: Bilirubin oxidase mutant, abbreviated Y121S/D370Y/L476P

<400> SEQUENCE: 41

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Ser Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Arg Gln Phe
            340                 345                 350

Arg Phe Gly Arg Thr Gly Pro Thr Trp Thr Ile Asn Gly Val Ala Phe
        355                 360                 365

Ala Tyr Val Gln Asn Arg Leu Leu Ala Asn Val Pro Val Gly Thr Val
```

```
                370             375             380
Glu Arg Trp Glu Leu Ile Asn Ala Gly Asn Gly Trp Thr His Pro Ile
385             390             395             400

His Ile His Leu Val Asp Phe Lys Val Ile Ser Arg Thr Ser Gly Asn
            405             410             415

Asn Ala Arg Thr Val Met Pro Tyr Glu Ser Gly Leu Lys Asp Val Val
            420             425             430

Trp Leu Gly Arg Arg Glu Thr Val Val Glu Ala His Tyr Ala Pro
            435             440             445

Phe Pro Gly Val Tyr Met Phe His Cys His Asn Leu Ile His Glu Asp
            450             455             460

His Asp Met Met Ala Ala Phe Asn Ala Thr Val Pro Pro Asp Tyr Gly
465             470             475             480

Tyr Asn Ala Thr Val Phe Val Asp Pro Met Glu Glu Leu Trp Gln Ala
            485             490             495

Arg Pro Tyr Glu Leu Gly Glu Phe Gln Ala Gln Ser Gly Gln Phe Ser
            500             505             510

Val Gln Ala Val Thr Glu Arg Ile Gln Thr Met Ala Glu Tyr Arg Pro
            515             520             525

Tyr Ala Ala Ala Asp Glu
            530

<210> SEQ ID NO 42
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A185S/A264V/L476P

<400> SEQUENCE: 42

Val Ala Gln Ile Ser Pro Gln Tyr Pro Met Phe Thr Val Pro Leu Pro
1               5               10              15

Ile Pro Pro Val Lys Gln Pro Arg Leu Thr Val Thr Asn Pro Val Asn
            20              25              30

Gly Gln Glu Ile Trp Tyr Tyr Glu Val Glu Ile Lys Pro Phe Thr His
            35              40              45

Gln Val Tyr Pro Asp Leu Gly Ser Ala Asp Leu Val Gly Tyr Asp Gly
        50              55              60

Met Ser Pro Gly Pro Thr Phe Gln Val Pro Arg Gly Val Glu Thr Val
65              70              75              80

Val Arg Phe Ile Asn Asn Ala Glu Ala Pro Asn Ser Val His Leu His
            85              90              95

Gly Ser Phe Ser Arg Ala Ala Phe Asp Gly Trp Ala Glu Asp Ile Thr
            100             105             110

Glu Pro Gly Ser Phe Lys Asp Tyr Tyr Pro Asn Arg Gln Ser Ala
            115             120             125

Arg Thr Leu Trp Tyr His Asp His Ala Met His Ile Thr Ala Glu Asn
            130             135             140

Ala Tyr Arg Gly Gln Ala Gly Leu Tyr Met Leu Thr Asp Pro Ala Glu
145             150             155             160

Asp Ala Leu Asn Leu Pro Ser Gly Tyr Gly Glu Phe Asp Ile Pro Met
            165             170             175

Ile Leu Thr Ser Lys Gln Tyr Thr Ser Asn Gly Asn Leu Val Thr Thr
            180             185             190

Asn Gly Glu Leu Asn Ser Phe Trp Gly Asp Val Ile His Val Asn Gly
```

```
                195                 200                 205
Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
                515                 520                 525

Tyr Ala Ala Ala Asp Glu
                530

<210> SEQ ID NO 43
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated F225V/D322N/M468V

<400> SEQUENCE: 43

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
```

```
                  20                  25                  30
Gly Gln Glu Ile Trp Tyr Tyr Glu Val Glu Ile Lys Pro Phe Thr His
            35                  40                  45
Gln Val Tyr Pro Asp Leu Gly Ser Ala Asp Leu Val Gly Tyr Asp Gly
     50                  55                  60
Met Ser Pro Gly Pro Thr Phe Gln Val Pro Arg Gly Val Glu Thr Val
 65                  70                  75                  80
Val Arg Phe Ile Asn Asn Ala Glu Ala Pro Asn Ser Val His Leu His
                85                  90                  95
Gly Ser Phe Ser Arg Ala Ala Phe Asp Gly Trp Ala Glu Asp Ile Thr
            100                 105                 110
Glu Pro Gly Ser Phe Lys Asp Tyr Tyr Pro Asn Arg Gln Ser Ala
        115                 120                 125
Arg Thr Leu Trp Tyr His Asp His Ala Met His Ile Thr Ala Glu Asn
        130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
                165                 170                 175
Ile Leu Thr Ser Lys Gln Tyr Thr Ala Asn Gly Asn Leu Val Thr Thr
            180                 185                 190
Asn Gly Glu Leu Asn Ser Phe Trp Gly Asp Val Ile His Val Asn Gly
            195                 200                 205
Gln Pro Trp Pro Phe Lys Asn Val Glu Pro Arg Lys Tyr Arg Phe Arg
        210                 215                 220
Val Leu Asp Ala Ala Val Ser Arg Ser Phe Gly Leu Tyr Phe Ala Asp
225                 230                 235                 240
Thr Asp Ala Ile Asp Thr Arg Leu Pro Phe Lys Val Ile Ala Ser Asp
                245                 250                 255
Ser Gly Leu Leu Glu His Pro Ala Asp Thr Ser Leu Leu Tyr Ile Ser
            260                 265                 270
Met Ala Glu Arg Tyr Glu Val Val Phe Asp Phe Ser Asp Tyr Ala Gly
        275                 280                 285
Lys Thr Ile Glu Leu Arg Asn Leu Gly Gly Ser Ile Gly Gly Ile Gly
        290                 295                 300
Thr Asp Thr Asp Tyr Asp Asn Thr Asp Lys Val Met Arg Phe Val Val
305                 310                 315                 320
Ala Asn Asp Thr Thr Gln Pro Asp Thr Ser Val Val Pro Ala Asn Leu
                325                 330                 335
Arg Asp Val Pro Phe Pro Ser Pro Thr Thr Asn Thr Pro Arg Gln Phe
            340                 345                 350
Arg Phe Gly Arg Thr Gly Pro Thr Trp Thr Ile Asn Gly Val Ala Phe
        355                 360                 365
Ala Asp Val Gln Asn Arg Leu Leu Ala Asn Val Pro Gly Thr Val
        370                 375                 380
Glu Arg Trp Glu Leu Ile Asn Ala Gly Asn Gly Trp Thr His Pro Ile
385                 390                 395                 400
His Ile His Leu Val Asp Phe Lys Val Ile Ser Arg Thr Ser Gly Asn
                405                 410                 415
Asn Ala Arg Thr Val Met Pro Tyr Glu Ser Gly Leu Lys Asp Val Val
            420                 425                 430
Trp Leu Gly Arg Arg Glu Thr Val Val Val Glu Ala His Tyr Ala Pro
        435                 440                 445
```

```
Phe Pro Gly Val Tyr Met Phe His Cys His Asn Leu Ile His Glu Asp
    450                 455                 460

His Asp Met Val Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 44
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated F225V/D370Y/L476P

<400> SEQUENCE: 44

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Gly Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Val Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270
```

```
Met Ala Glu Arg Tyr Glu Val Phe Asp Phe Ser Asp Tyr Ala Gly
            275                 280                 285

Lys Thr Ile Glu Leu Arg Asn Leu Gly Gly Ser Ile Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Tyr Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 45
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V/R356L/L476P

<400> SEQUENCE: 45

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95
```

```
Gly Ser Phe Ser Arg Ala Ala Phe Asp Gly Trp Ala Glu Asp Ile Thr
                100                 105                 110

Glu Pro Gly Ser Phe Lys Asp Tyr Tyr Pro Asn Arg Gln Ser Ala
            115                 120                 125

Arg Thr Leu Trp Tyr His Asp His Ala Met His Ile Thr Ala Glu Asn
        130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
            195                 200                 205

Gln Pro Trp Pro Phe Lys Asn Val Glu Pro Arg Lys Tyr Arg Phe Arg
            210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Leu Thr Gly Pro Thr Trp Thr Ile Asn Gly Val Ala Phe
            355                 360                 365

Ala Asp Val Gln Asn Arg Leu Leu Ala Asn Val Pro Val Gly Thr Val
        370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
            450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525
```

Tyr Ala Ala Ala Asp Glu
    530

<210> SEQ ID NO 46
<211> LENGTH: 34
<212> TYPE: DNA
<213> ORGANISM: Artificial
<220> FEATURE:
<223> OTHER INFORMATION: Synthesized: Forward primer for BO cDNA
      amplification

<400> SEQUENCE: 46
gggaagctta tgttcaaaca cacacttgga gctg					34

<210> SEQ ID NO 47
<211> LENGTH: 34
<212> TYPE: DNA
<213> ORGANISM: Artificial
<220> FEATURE:
<223> OTHER INFORMATION: Synthesized: Reverse primer for BO cDNA
      amplification

<400> SEQUENCE: 47
gggtctagac tcgtcagctg cggcgtaagg tctg					34

<210> SEQ ID NO 48
<211> LENGTH: 1719
<212> TYPE: DNA
<213> ORGANISM: Myrothecium verrucaria

<400> SEQUENCE: 48

| | | | | | |
|---|---|---|---|---|---|
| atgttcaaac | acacacttgg | agctgctgcc | ctcagcttgc | tttcaacag | caatgctgtc | 60 |
| caggcaagcc | ccgtccccga | gacctcaccg | gcaactggac | atctcttcaa | gcgagttgcc | 120 |
| cagatcagcc | cacagtatcc | catgttcaca | gtaccactgc | caattcctcc | tgttaagcag | 180 |
| ccccgcttga | ctgtaaccaa | tcctgtgaat | ggacaagaga | tctggtacta | tgaggtcgag | 240 |
| atcaagccct | tcactcacca | ggtttaccct | gaccttggat | ccgctgatct | ggtcgggtac | 300 |
| gatggaatgt | ctcctggccc | tacttttcag | gttcctcgtg | gagttgaaac | agttgtccgc | 360 |
| ttcattaaca | atgctgaggc | tcctaactct | gttcacttgc | acggatcatt | ctctcgtgcc | 420 |
| gcctttgacg | gatgggcaga | ggacatcacc | gagcctggca | gcttcaaaga | ctattactac | 480 |
| ccaaacagac | agtctgcccg | taccctatgg | taccacgatc | atgctatgca | tatcactgct | 540 |
| gagaacgcct | accgtggcca | ggctggtctc | tacatgctca | ctgacccagc | cgaagacgct | 600 |
| ctcaacttgc | caagtggata | tggcgagttc | gatattccaa | tgatcctcac | gtctaagcaa | 660 |
| tacaccgcaa | acggcaactt | ggtcaccact | aatggagagc | tgaactcatt | ctggggtgat | 720 |
| gtaattcacg | tgaacggtca | accctggcct | ttcaagaacg | ttgagcctcg | caaatatcga | 780 |
| ttccgcttcc | tcgatgccgc | agtttctcgc | tctttcggcc | tttactttgc | tgatactgat | 840 |
| gctatcgaca | ctcgcttgcc | tttcaaggtt | attgcctccg | attctggtct | tcttgaacac | 900 |
| cctgccgata | ccagcttgct | gtacatttcc | atggccgagc | gttacgaagt | tgtgtttgac | 960 |
| ttctccgact | atgctggcaa | gactattgaa | ctccgcaacc | tgggcggcag | cattggcggc | 1020 |
| attggaacag | ataccgacta | tgataacacc | gacaaggtca | tgcgtttcgt | ggtagcagac | 1080 |
| gacacaactc | agccagatac | ctcagttgtt | cctgctaacc | ttcgtgatgt | tcccttcccc | 1140 |
| tctcccacca | caaacacccc | ccgacagttc | gctttggtc | gcaccggtcc | tacctggact | 1200 |
| attaatggtg | ttgcttttgc | tgatgttcaa | aaccgtctgc | ttgcaaacgt | acccgttggt | 1260 |

```
actgtcgagc gttgggagct catcaacgcc ggtaacggtt ggacgcaccc tattcacatc    1320
catcttgtcg acttcaaggt catttctcgt acttccggca acaacgcgcg cacagtcatg    1380
ccatacgagt ccggtctcaa agacgttgtc tggcttggtc gccgtgaaac tgtggttgtt    1440
gaggctcatt acgcgccttt ccctggtgta tacatgttcc attgccacaa tttgattcac    1500
gaggatcacg atatgatggc tgcctttaac gccaccgtcc tgccagatta tggctataat    1560
gccactgttt tcgttgaccc tatggaagag ctttggcagg ctcgtcccta tgaactcggc    1620
gagttccagg ctcagagtgg ccagttcagc gttcaggctg ttactgagcg tatccagact    1680
atggctgaat acagaccttca cgccgcagct gacgagtag                          1719
```

<210> SEQ ID NO 49
<211> LENGTH: 18
<212> TYPE: DNA
<213> ORGANISM: Artificial
<220> FEATURE:
<223> OTHER INFORMATION: Synthesized: Upstream sequence of the insert
      site of the plasmid vector

<400> SEQUENCE: 49
attaagaaat gttcaaac                                                   18

<210> SEQ ID NO 50
<211> LENGTH: 19
<212> TYPE: DNA
<213> ORGANISM: Artificial
<220> FEATURE:
<223> OTHER INFORMATION: Synthesized: Modified upstream sequence of the
      insert site of the plasmid vector

<400> SEQUENCE: 50
attaagaaaa tgttcaaac                                                  19

<210> SEQ ID NO 51
<211> LENGTH: 39
<212> TYPE: DNA
<213> ORGANISM: Artificial
<220> FEATURE:
<223> OTHER INFORMATION: Synthesized: Forward primer for modification of
      upstream sequence of the insert site

<400> SEQUENCE: 51
ctatagggaa tattaagaaa atgttcaaac acacacttg                            39

<210> SEQ ID NO 52
<211> LENGTH: 41
<212> TYPE: DNA
<213> ORGANISM: Artificial
<220> FEATURE:
<223> OTHER INFORMATION: Synthesized: Reverse primer for modification of
      upstream sequence of the insert site

<400> SEQUENCE: 52
caagtgtgtg tttgaacatt ttcttaatat tccctatagt g                         41

<210> SEQ ID NO 53
<211> LENGTH: 33
<212> TYPE: DNA
<213> ORGANISM: Artificial
<220> FEATURE:
<223> OTHER INFORMATION: Synthesized: Forward primer for error-prone PCR

<400> SEQUENCE: 53
gtaaccaatc ctgtgaatgg acaagagatc tgg                                  33

```
<210> SEQ ID NO 54
<211> LENGTH: 35
<212> TYPE: DNA
<213> ORGANISM: Artificial
<220> FEATURE:
<223> OTHER INFORMATION: Synthesized: Reverse primer for error-prone PCR

<400> SEQUENCE: 54
gggataggct taccttcgaa gggccctcta gactc                              35

<210> SEQ ID NO 55
<211> LENGTH: 32
<212> TYPE: DNA
<213> ORGANISM: Artificial
<220> FEATURE:
<223> OTHER INFORMATION: Synthesized: Forward primer for amplification
      of the inserted BO gene

<400> SEQUENCE: 55
gggaattctt gcccagatca gcccacagta tc                                 32

<210> SEQ ID NO 56
<211> LENGTH: 32
<212> TYPE: DNA
<213> ORGANISM: Artificial
<220> FEATURE:
<223> OTHER INFORMATION: Synthesized: Reverse primer for amplification
      of the inserted BO gene

<400> SEQUENCE: 56
gggactagtc actcgtcagc tgcggcgtaa gg                                 32

<210> SEQ ID NO 57
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A103P

<400> SEQUENCE: 57
```

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Pro Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met

```
                      165                 170                 175
Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
            195                 200                 205

Gln Pro Trp Pro Phe Lys Asn Val Glu Pro Arg Lys Tyr Arg Phe Arg
        210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
        290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
        370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
        450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 58
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated Y270D
```

-continued

```
<400> SEQUENCE: 58

Val Ala Gln Ile Ser Pro Gln Tyr Pro Met Phe Thr Val Pro Leu Pro
 1               5                  10                  15

Ile Pro Pro Val Lys Gln Pro Arg Leu Thr Val Thr Asn Pro Val Asn
             20                  25                  30

Gly Gln Glu Ile Trp Tyr Tyr Glu Val Glu Ile Lys Pro Phe Thr His
         35                  40                  45

Gln Val Tyr Pro Asp Leu Gly Ser Ala Asp Leu Val Gly Tyr Asp Gly
     50                  55                  60

Met Ser Pro Gly Pro Thr Phe Gln Val Pro Arg Gly Val Glu Thr Val
 65                  70                  75                  80

Val Arg Phe Ile Asn Asn Ala Glu Ala Pro Asn Ser Val His Leu His
                 85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Asp Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Thr Thr Asn Thr Pro Arg Gln Phe
        340                 345                 350

Arg Phe Gly Arg Thr Gly Pro Thr Trp Thr Ile Asn Gly Val Ala Phe
    355                 360                 365

Ala Asp Val Gln Asn Arg Leu Leu Ala Asn Val Pro Val Gly Thr Val
370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415
```

```
Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
            435                 440                 445

Phe Pro Gly Val Tyr Met Phe His Cys His Asn Leu Ile His Glu Asp
            450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
            515                 520                 525

Tyr Ala Ala Ala Asp Glu
            530

<210> SEQ ID NO 59
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated S299N

<400> SEQUENCE: 59

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
            115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240
```

```
Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Asn Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gly Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 60
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated V381L

<400> SEQUENCE: 60

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60
```

```
Met Ser Pro Gly Pro Thr Phe Gln Val Pro Arg Val Glu Thr Val
 65                  70                  75                  80

Val Arg Phe Ile Asn Asn Ala Glu Ala Pro Asn Ser Val His Leu His
                 85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Leu Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495
```

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
        530

<210> SEQ ID NO 61
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A418T

<400> SEQUENCE: 61

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

```
Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Thr Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 62
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated R437H

<400> SEQUENCE: 62

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140
```

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg His Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Leu Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 63
<211> LENGTH: 534
<212> TYPE: PRT

<213> ORGANISM: Artificial
<220> FEATURE:
<223> OTHER INFORMATION: Synthesized: Bilirubin oxidase mutant,
      abbreviated A264/S299N/L476P

<400> SEQUENCE: 63

```
Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Asn Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
```

```
            385                 390                 395                 400
His Ile His Leu Val Asp Phe Lys Val Ile Ser Arg Thr Ser Gly Asn
            405                 410                 415
Asn Ala Arg Thr Val Met Pro Tyr Glu Ser Gly Leu Lys Asp Val Val
            420                 425                 430
Trp Leu Gly Arg Arg Glu Thr Val Val Glu Ala His Tyr Ala Pro
            435                 440                 445
Phe Pro Gly Val Tyr Met Phe His Cys His Asn Leu Ile His Glu Asp
            450                 455                 460
His Asp Met Met Ala Ala Phe Asn Ala Thr Val Pro Pro Asp Tyr Gly
465                 470                 475                 480
Tyr Asn Ala Thr Val Phe Val Asp Pro Met Glu Glu Leu Trp Gln Ala
            485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
            515                 520                 525
Tyr Ala Ala Ala Asp Glu
            530

<210> SEQ ID NO 64
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264/V381L/L476P

<400> SEQUENCE: 64

Val Ala Gln Ile Ser Pro Gln Tyr Pro Met Phe Thr Val Pro Leu Pro
1               5                   10                  15
Ile Pro Pro Val Lys Gln Pro Arg Leu Thr Val Thr Asn Pro Val Asn
            20                  25                  30
Gly Gln Glu Ile Trp Tyr Tyr Glu Val Glu Ile Lys Pro Phe Thr His
        35                  40                  45
Gln Val Tyr Pro Asp Leu Gly Ser Ala Asp Leu Val Gly Tyr Asp Gly
    50                  55                  60
Met Ser Pro Gly Pro Thr Phe Gln Val Pro Arg Gly Val Glu Thr Val
65                  70                  75                  80
Val Arg Phe Ile Asn Asn Ala Glu Ala Pro Asn Ser Val His Leu His
            85                  90                  95
Gly Ser Phe Ser Arg Ala Ala Phe Asp Gly Trp Ala Glu Asp Ile Thr
        100                 105                 110
Glu Pro Gly Ser Phe Lys Asp Tyr Tyr Pro Asn Arg Gln Ser Ala
    115                 120                 125
Arg Thr Leu Trp Tyr His Asp His Ala Met His Ile Thr Ala Glu Asn
130                 135                 140
Ala Tyr Arg Gly Gln Ala Gly Leu Tyr Met Leu Thr Asp Pro Ala Glu
145                 150                 155                 160
Asp Ala Leu Asn Leu Pro Ser Gly Tyr Gly Glu Phe Asp Ile Pro Met
            165                 170                 175
Ile Leu Thr Ser Lys Gln Tyr Thr Ala Asn Gly Asn Leu Val Thr Thr
        180                 185                 190
Asn Gly Glu Leu Asn Ser Phe Trp Gly Asp Val Ile His Val Asn Gly
    195                 200                 205
Gln Pro Trp Pro Phe Lys Asn Val Glu Pro Arg Lys Tyr Arg Phe Arg
```

```
                   210                 215                 220
Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Leu Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
                450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Gly Tyr Arg Pro
                515                 520                 525

Tyr Ala Ala Ala Asp Glu
                530

<210> SEQ ID NO 65
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V/A418T/L476P

<400> SEQUENCE: 65

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
```

-continued

```
                35                  40                  45
Gln Val Tyr Pro Asp Leu Gly Ser Ala Asp Leu Val Gly Tyr Asp Gly
 50                  55                  60

Met Ser Pro Gly Pro Thr Phe Gln Val Pro Arg Gly Val Glu Thr Val
 65                  70                  75                  80

Val Arg Phe Ile Asn Asn Ala Glu Ala Pro Asn Ser Val His Leu His
                 85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Pro Asn Arg Gln Ser Ala
                115                 120                 125

Arg Thr Leu Trp Tyr His Asp His Ala Met His Ile Thr Ala Glu Asn
130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
                260                 265                 270

Met Ala Glu Arg Tyr Glu Val Val Phe Asp Phe Ser Asp Tyr Ala Gly
                275                 280                 285

Lys Thr Ile Glu Leu Arg Asn Leu Gly Gly Ser Ile Gly Gly Ile Gly
290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Thr Arg Thr Val Met Pro Tyr Glu Ser Gly Leu Lys Asp Val Val
                420                 425                 430

Trp Leu Gly Arg Arg Glu Thr Val Val Glu Ala His Tyr Ala Pro
                435                 440                 445

Phe Pro Gly Val Tyr Met Phe His Cys His Asn Leu Ile His Glu Asp
450                 455                 460
```

```
His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510

Val Gln Ala Val Thr Glu Arg Ile Gln Thr Met Ala Glu Tyr Arg Pro
        515                 520                 525

Tyr Ala Ala Ala Asp Glu
    530

<210> SEQ ID NO 66
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A264V/R437H/L476P

<400> SEQUENCE: 66

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

Gly Gln Glu Ile Trp Tyr Tyr Glu Val Glu Ile Lys Pro Phe Thr His
        35                  40                  45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
            100                 105                 110

Glu Pro Gly Ser Phe Lys Asp Tyr Tyr Tyr Pro Asn Arg Gln Ser Ala
        115                 120                 125

Arg Thr Leu Trp Tyr His Asp His Ala Met His Ile Thr Ala Glu Asn
    130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Tyr Ile Ser
            260                 265                 270

Met Ala Glu Arg Tyr Glu Val Val Phe Asp Phe Ser Asp Tyr Ala Gly
        275                 280                 285
```

```
Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg His Glu Thr Val Val Glu Ala His Tyr Ala Pro
    435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
                500                 505                 510

Val Gln Ala Val Thr Glu Arg Ile Gln Thr Met Ala Glu Tyr Arg Pro
                515                 520                 525

Tyr Ala Ala Ala Asp Glu
        530

<210> SEQ ID NO 67
<211> LENGTH: 534
<212> TYPE: PRT
<213> ORGANISM: Artificial
<220> FEATURE:
<223> OTHER INFORMATION: Synthesized: Bilirubin oxidase mutant,
      abbreviated A103P/A264V/Y270D/L476P

<400> SEQUENCE: 67

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
                20                  25                  30

Gly Gln Glu Ile Trp Tyr Tyr Glu Val Glu Ile Lys Pro Phe Thr His
            35                  40                  45

Gln Val Tyr Pro Asp Leu Gly Ser Ala Asp Leu Val Gly Tyr Asp Gly
        50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Pro Phe Asp Gly Trp Ala Glu Asp Ile Thr
            100                 105                 110
```

```
Glu Pro Gly Ser Phe Lys Asp Tyr Tyr Tyr Pro Asn Arg Gln Ser Ala
            115                 120                 125

Arg Thr Leu Trp Tyr His Asp His Ala Met His Ile Thr Ala Glu Asn
        130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
            180                 185                 190

Asn Gly Glu Leu Asn Ser Phe Trp Gly Asp Val Ile His Val Asn Gly
        195                 200                 205

Gln Pro Trp Pro Phe Lys Asn Val Glu Pro Arg Lys Tyr Arg Phe Arg
    210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Val Asp Thr Ser Leu Leu Asp Ile Ser
            260                 265                 270

Met Ala Glu Arg Tyr Glu Val Val Phe Asp Phe Ser Asp Tyr Ala Gly
        275                 280                 285

Lys Thr Ile Glu Leu Arg Asn Leu Gly Gly Ser Ile Gly Gly Ile Gly
    290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
            340                 345                 350

Arg Phe Gly Arg Thr Gly Pro Thr Trp Thr Ile Asn Gly Val Ala Phe
        355                 360                 365

Ala Asp Val Gln Asn Arg Leu Leu Ala Asn Val Pro Val Gly Thr Val
    370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
            420                 425                 430

Trp Leu Gly Arg Arg Glu Thr Val Val Glu Ala His Tyr Ala Pro
        435                 440                 445

Phe Pro Gly Val Tyr Met Phe His Cys His Asn Leu Ile His Glu Asp
    450                 455                 460

His Asp Met Met Ala Ala Phe Asn Ala Thr Val Pro Pro Asp Tyr Gly
465                 470                 475                 480

Tyr Asn Ala Thr Val Phe Val Asp Pro Met Glu Glu Leu Trp Gln Ala
                485                 490                 495

Arg Pro Tyr Glu Leu Gly Glu Phe Gln Ala Gln Ser Gly Gln Phe Ser
            500                 505                 510
```

```
Val Gln Ala Val Thr Glu Arg Ile Gln Thr Met Ala Glu Tyr Arg Pro
        515                 520                 525

Tyr Ala Ala Ala Asp Glu
    530
```

BILIRUBIN OXIDASE MUTANT HAVING THERMAL STABILITY

CROSS REFERENCES TO RELATED APPLICATIONS

The present application is a continuation-in-part of application Ser. No. 11/946,543 filed on Nov. 28, 2007, which claims priority to Japanese Patent Applications JP 2006-330352 and JP 2007-160964 filed in the Japan Patent Office on Dec. 7, 2006 and Jun. 19, 2007, respectively, the entire contents of which is being incorporated herein by reference.

BACKGROUND

The present application relates to a bilirubin oxidase mutant having thermal stability. More specifically, the present application relates to a bilirubin oxidase mutant having prescribed levels or more of heat resistance in addition to enzymatic activity and its contribution to the durability of a biocathode in an enzymatic fuel cell.

An "enzyme" is a biocatalyst for allowing many reactions relative to the maintenance of life to smoothly proceed under a mild condition in vivo. This enzyme turns over in vivo, is produced in vivo depending on the situation and exhibits its catalytic function.

At present, technologies for utilizing this enzyme in vitro have already been put into practical use or studied towards practical implementation. For example, a technology for utilizing an enzyme has been developed in various technical fields such as the production of a useful substance, the production, measurement or analysis of energy-related substance, the environmental preservation and the medical treatment. In relatively recent years, technologies regarding an enzyme cell which is one kind of a fuel cell (see, for example, JP-A-2004-71559), an enzyme electrode, an enzyme sensor (a sensor for measuring a chemical substance utilizing an enzymatic reaction) and the like have also been proposed.

Since a chemical main body of this enzyme is a protein, the enzyme has properties that it is denatured by the degree of heat or pH. For that reason, enzymes have low stability in vitro as compared with other chemical catalysts such as metal catalysts. Accordingly, when an enzyme is utilized in vitro, it is important to allow the enzyme to work more stably in response to an environmental change and to maintain an activity thereof.

When an enzyme is utilized in vitro, approaches such as a method for artificially modifying the nature or function of the enzyme itself and a method for devising the environment of a site where the enzyme works are employed. With respect to the former method, it is generally carried out that the base sequence of a gene encoding a protein is artificially modified, the thus modified gene is expressed in an organism such as *Escherichia coli* to produce an artificially mutated protein, and the protein mutant having functions and natures adapted to the use purpose is then subjected to separation (screening) (see, for example, JP-A-2004-298185).

The "bilirubin oxidase" as referred to herein is an enzyme which catalyzes a reaction for oxidizing bilirubin into biliverdin and is one kind of enzyme belonging to a multicopper oxidase (a general term of an enzymes having plural copper ions in the active center). This enzyme has hitherto been widely used as an inspection reagent of liver function and the like (a measurement reagent of bilirubin in a blood serum) in the clinical laboratory examination. In recent years, this enzyme is also regarded as a catalyst for realizing an electrochemical four-electron reduction reaction of oxygen on a cathode side of the foregoing enzyme cell.

Under circumstances where expectations for utilizing this bilirubin oxidase in vitro are rising, a technology for investigating the same enzyme having more excellent thermal stability (see, for example, JP-A-2006-68003) and a technology for stably maintaining the enzymatic activity of the same enzyme over a longer period of time (see, for example, JP-A-2000-83661) have also been proposed.

In consideration of the utilization of a bilirubin oxidase in vitro, it is necessary that the thermal stability is more enhanced. However, this bilirubin oxidase involves a problem that the enzymatic activity is reduced to not more than 20% by heating at 60° C. for one hour. For example, in the field of an enzyme cell, since the bilirubin oxidase has the lowest thermal stability among a group of enzymes to be utilized and is remarkably low in the thermal stability as compared with enzymes on an anode side (for example, glucose dehydrogenase and diaphorase), it is not suitable to put an enzyme cell into practical use. Also, though there is a choice to substitute this bilirubin oxidase with laccase which is a multicopper oxidase, this laccase involves not only a problem regarding the heat resistance but a problem that the enzymatic activity at room temperature in a neutral pH region is remarkably low as compared with the bilirubin oxidase.

The durability of an enzymatic biofuel cell is generally determined by the stability of the immobilized enzyme on its electrode. There has been a focus on the extended active enzyme lifetimes at anode surfaces but limited studies on the stability of the cathode enzyme.

Bilirubin oxidase (BO, EC 1.3.3.5), which belongs to the sub-family of multicopper oxidase (MCO), has been widely employed as the cathode enzyme of an enzymatic biofuel cell, because this enzyme has higher activity than the other MCOs at neutral pH (4,6,7). Studies have shown that an enzymatic biofuel cell with BO reached the maximum power density of 5.0 mW/cm$^2$ at 0.5 V by the introduction of some new technologies (Sakai, H. et. al., Energy Environ. Sci. 2009, 2, 133; Sakai et. al., ECS Trans., 2009, 16(38), 9) and these studies demonstrated that a biofuel cell has power density enough to apply in practical use. The thermo-stability of BO, however, is much lower than that of the anode enzymes, and this is problematic for practical use as a biofuel cell.

SUMMARY

Then, in consideration of the wide applicability of a bilirubin oxidase in vitro, it is desirable to provide a bilirubin oxidase mutant having prescribed levels or more of enzymatic activity and heat resistance of a bilirubin oxidase.

According to an embodiment, there is provided a heat-resistant bilirubin oxidase mutant obtained by deletion, replacement, addition or insertion of at least one amino acid residue of the wild type amino sequence of SEQ. ID. No. 1 of a bilirubin oxidase derived from, an imperfect filamentous fungus, *Myrothecium verrucaria* (hereinafter referred to as "*M. verrucaria*") so as to have enhanced heat resistance, and more favorably a heat-resistant bilirubin oxidase mutant having, for example, a denaturation temperature $T_m$ value of 72° C. or higher. Furthermore, there is provided a heat-resistant bilirubin oxidase mutant in which a residual activity after heating at 60° C. for one hour is 20% or more. For example, there is provided a heat-resistant bilirubin oxidase mutant having amino acid sequences of SEQ. ID. Nos. 2 to 45 and 57 to 67. As the foregoing imperfect filamentous fungus, for example, a strain of *M. verrucaria* NBRC (IFO) 6113 can be employed. Also, when the heat-resistant bilirubin oxidase mutant is expressed by using a yeast, *Pichia methanolica* as a host, it is possible to achieve abundant expression.

Here, in a heat-resistant bilirubin oxidase mutant represented by SEQ. ID. No. 2, glutamine at the 49th position from the N-terminus of the wild type amino acid sequence of SEQ. ID. No. 1 is replaced with lysine (hereafter abbreviated as "Q49K"). Similarly, in a heat-resistant bilirubin oxidase mutant represented by SEQ. ID. No. 3, glutamine at the 72nd position is replaced with glutamic acid (hereafter abbreviated as "Q72E"); in a heat-resistant bilirubin oxidase mutant represented by SEQ. ID. No. 4, valine at the 81st position is replaced with leucine (hereafter abbreviated as "V81L"); in a heat-resistant bilirubin oxidase mutant represented by SEQ. ID. No. 5, tyrosine at the 121st position is replaced with serine (hereafter abbreviated as "Y121S"); in a heat-resistant bilirubin oxidase mutant represented by SEQ. ID. No. 6, arginine at the 147th position is replaced with proline (hereafter abbreviated as "R147P"); in a heat-resistant bilirubin oxidase mutant represented by SEQ. ID. No. 7, alanine at the 185th position is replaced with serine (hereafter abbreviated as "A185S"); in a heat-resistant bilirubin oxidase mutant represented by SEQ. ID. No. 8, proline at the 210th position is replaced with leucine (hereafter abbreviated as "P210L"); in a heat-resistant bilirubin oxidase mutant represented by SEQ. ID. No. 9, phenylalanine at the 225th position is replaced with valine (hereafter abbreviated as "F225V"); in a heat-resistant bilirubin oxidase mutant represented by SEQ. ID. No. 10, glycine at the 258th position is replaced with valine (hereafter abbreviated as "G258V"); in a heat-resistant bilirubin oxidase mutant represented by SEQ. ID. No. 11, alanine at the 264th position is replaced with valine (hereafter abbreviated as "A264V"); in a heat-resistant bilirubin oxidase mutant represented by SEQ. ID. No. 12, aspartic acid at the 322nd position is replaced with asparagine (hereafter abbreviated as "D322N"); in a heat-resistant bilirubin oxidase mutant represented by SEQ. ID. No. 13, asparagine at the 335th position is replaced with serine (hereafter abbreviated as "N335S"); in a heat-resistant bilirubin oxidase mutant represented by SEQ. ID. No. 14, arginine at the 356th position is replaced with leucine (hereafter abbreviated as "R356L"); in a heat-resistant bilirubin oxidase mutant represented by SEQ. ID. No. 15, proline at the 359th position is replaced with serine (hereafter abbreviated as "P359S"); in a heat-resistant bilirubin oxidase mutant represented by SEQ. ID. No. 16, aspartic acid at the 370th position is replaced with tyrosine (hereafter abbreviated as "D370Y"); in a heat-resistant bilirubin oxidase mutant represented by SEQ. ID. No. 17, valine at the 371st position is replaced with alanine (hereafter abbreviated as "V371A"); in a heat-resistant bilirubin oxidase mutant represented by SEQ. ID. No. 18, proline at the 423rd position is replaced with leucine (hereafter abbreviated as "P423L"); in a heat-resistant bilirubin oxidase mutant represented by SEQ. ID. No. 19, methionine at the 468th position is replaced with valine (hereafter abbreviated as "M468V"); in a heat-resistant bilirubin oxidase mutant represented by SEQ. ID. No. 20, leucine at the 476th position is replaced with proline (hereafter abbreviated as "L476P"); and in a heat-resistant bilirubin oxidase mutant represented by SEQ. ID. No. 21, valine at the 513rd position is replaced with leucine (hereafter abbreviated as "V513L").

Also, in a heat-resistant bilirubin oxidase mutant represented by SEQ. ID. No. 57, alanine at the 103rd position is replaced with proline (hereafter abbreviated as "A103P"); in a heat-resistant bilirubin oxidase mutant represented by SEQ. ID. No. 58, tyrosine at the 270th position is replaced with aspartic acid (hereafter abbreviated as "Y270D"); in a heat-resistant bilirubin oxidase mutant represented by SEQ. ID. No. 59, serine at the 299th position is replaced with asparagine (hereafter abbreviated as "S299N"); in a heat-resistant bilirubin oxidase mutant represented by SEQ. ID. No. 60, valine at the 381st position is replaced with leucine (hereafter abbreviated as "V381L"); in a heat-resistant bilirubin oxidase mutant represented by SEQ. ID. No. 61, alanine at the 418th position is replaced with threonine (hereafter abbreviated as "A418T"); and in a heat-resistant bilirubin oxidase mutant represented by SEQ. ID. No. 62, arginine at the 437th position is replaced with histidine (hereafter abbreviated as "R437H").

Also, in a heat-resistant bilirubin oxidase mutant represented by SEQ. ID. No. 22, glutamine at the 49th position from the N-terminus of the wild type amino acid sequence of SEQ. ID. No. 1 is replaced with lysine, and valine at the 371st position is replaced with alanine (hereafter abbreviated as "Q49K/V371A"). Similarly, in a heat-resistant bilirubin oxidase mutant represented by SEQ. ID. No. 23, glutamine at the 72nd position is replaced with glutamic acid, and proline at the 210th position is replaced with leucine (hereafter abbreviated as "Q72E/P210L"); in a heat-resistant bilirubin oxidase mutant represented by SEQ. ID. No. 24, glutamine at the 72nd position is replaced with glutamic acid, and alanine at the 264th position is replaced with valine (hereafter abbreviated as "Q72E/A264V"); in a heat-resistant bilirubin oxidase mutant represented by SEQ. ID. No. 25, valine at the 81st position is replaced with leucine, and arginine at the 147th position is replaced with proline (hereafter abbreviated as "V81L/R147P"); in a heat-resistant bilirubin oxidase mutant represented by SEQ. ID. No. 26, valine at the 81st position is replaced with leucine, and proline at the 423rd position is replaced with leucine (hereafter abbreviated as "V81L/P423L"); in a heat-resistant bilirubin oxidase mutant represented by SEQ. ID. No. 27, tyrosine at the 121st position is replaced with serine, and leucine at the 476th position is replaced with proline (hereafter abbreviated as "Y121S/L476P"); in a heat-resistant bilirubin oxidase mutant represented by SEQ. ID. No. 28, alanine at the 185th position is replaced with serine, and glycine at the 258th position is replaced with valine (hereafter abbreviated as "A185S/G258V"); in a heat-resistant bilirubin oxidase mutant represented by SEQ. ID. No. 29, proline at the 210th position is replaced with leucine, and alanine at the 264th position is replaced with valine (hereafter abbreviated as "P210L/A264V"); in a heat-resistant bilirubin oxidase mutant represented by SEQ. ID. No. 30, phenylalanine at the 225th position is replaced with valine, and aspartic acid at the 322nd position is replaced with asparagine (hereafter abbreviated as "F225V/D322N"); in a heat-resistant bilirubin oxidase mutant represented by SEQ. ID. No. 31, phenylalanine at 225th position is replaced by valine, and leucine at the 476th position is replaced with proline (hereafter abbreviated as "F225V/L476P"); in a heat-resistant bilirubin oxidase mutant represented by SEQ. ID. No. 32, alanine at the 264th position is replaced with valine, and arginine at the 356th position is replaced with leucine (hereafter abbreviated as "A264V/R356L"); in a heat-resistant bilirubin oxidase mutant represented by SEQ. ID. No. 33, alanine at the 264th position is replaced with valine, and leucine at the 476th position is replaced with proline (hereafter abbreviated as "A264V/L476P"); in a heat-resistant bilirubin oxidase mutant represented by SEQ. ID. No. 34, aspartic acid at the 322nd position is replaced with asparagine, and methionine at the 468th position is replaced with valine (hereafter abbreviated as "D322N/M468V"); in a heat-resistant bilirubin oxidase mutant represented by SEQ. ID. No. 35, asparagine at the 335th position is replaced with serine, and proline at the 423rd position is replaced with leucine (hereafter abbreviated as "N335S/P423L"); in a heat-resistant bilirubin oxidase mutant represented by SEQ. ID. No. 36, arginine at the 356th position is replaced with leucine, and leucine at the 476th position is replaced with proline (hereafter abbreviated as "R356L/L476P"); and in a heat-resistant bilirubin oxidase mutant represented by SEQ. ID. No. 37, valine at the 371st position is replaced with alanine, and valine at the 513rd position is replaced with leucine (hereafter abbreviated as "V371A/V513L").

Furthermore, in a heat-resistant bilirubin oxidase mutant represented by SEQ. ID. No. 38, glutamine at the 49th position from the N-terminus of the wild type amino acid sequence of SEQ. ID. No. 1 is replaced with lysine, valine at the 371st position is replaced with alanine, and valine at the 513rd position is replaced with leucine (hereafter abbreviated as "Q49K/V371A/V513L"). Similarly, in a heat-resistant bilirubin oxidase mutant represented by SEQ. ID. No. 39, glutamine at the 72nd position is replaced with glutamic acid, proline at the 210th position is replaced with leucine, and alanine at the 264th position is replaced with valine (hereafter abbreviated as "Q72E/P210L/A264V"); in a heat-resistant bilirubin oxidase mutant represented by SEQ. ID. No. 40, valine at the 81st position is replaced with leucine, asparagine at the 335th position is replaced with serine, and proline at the 423rd position is replaced with leucine (hereafter abbreviated as "V81L/N335S/P423L"); in a heat-resistant bilirubin oxidase mutant represented by SEQ. ID. No. 41, tyrosine at the 121st position is replaced with serine, aspartic acid at the 370th position is replaced with tyrosine, and leucine at the 476th position is replaced with proline (hereafter abbreviated as "Y121S/D370Y/L476P"); in a heat-resistant bilirubin oxidase mutant represented by SEQ. ID. No. 42, alanine at the 185th position is replaced with serine, alanine at the 264th position is replaced with valine, and leucine at the 476th position is replaced with proline (hereafter abbreviated as "A185S/A264V/L476P"); in a heat-resistant bilirubin oxidase mutant represented by SEQ. ID. No. 43, phenylalanine at the 225th position is replaced with valine, aspartic acid at the 322nd position is replaced with asparagine, and methionine at the 468th position is replaced with valine (hereafter abbreviated as "F225V/D322N/M468V"); in a heat-resistant bilirubin oxidase mutant represented by SEQ. ID. No. 44, phenylalanine at the 225th position is replaced with valine, aspartic acid at the 370th position is replaced with tyrosine, and leucine at the 476th position is replaced with proline (hereafter abbreviated as "F225V/D370Y/L476P"); and in a heat-resistant bilirubin oxidase mutant represented by SEQ. ID. No. 45, alanine at the 264th position is replaced with valine, arginine at the 356th position is replaced with leucine, and leucine at the 476th position is replaced with proline (hereafter abbreviated as "A264V/R356L/L476P"). Also, in a heat-resistant bilirubin oxidase mutant represented by SEQ. ID. No. 63, alanine at the 264th position is replaced with valine, serine at the 299th position is replaced with asparagine, and leucine at the 476th position is replaced with proline (hereinafter abbreviated as "A264V/S299N/L476P"); in a heat-resistant bilirubin oxidase mutant represented by SEQ. ID. No. 64, alanine at the 264th position is replaced with valine, valine at the 381st position is replaced with leucine, and leucine at the 476th position is replaced with proline (hereinafter abbreviated as "A264V/V381L/L476P"); in a heat-resistant bilirubin oxidase mutant represented by SEQ. ID. No. 65, alanine at the 264th position is replaced with valine, alanine at the 418th position is replaced with threonine, and leucine at the 476th position is replaced with proline (hereinafter abbreviated as "A264V/A418T/L476P"); and in a heat-resistant bilirubin oxidase mutant represented by SEQ. ID. No. 66, alanine at the 264th position is replaced with valine, arginine at the 437th position is replaced with histidine, and leucine at the 476th position is replaced with proline (hereinafter abbreviated as "A264V/R437H/L476P"). Furthermore, in a heat-resistant bilirubin oxidase mutant represented by SEQ. ID. No. 67, alanine at the 103rd position is replaced with proline, alanine at the 264th position is replaced with valine, tyrosine at the 270th position is replaced with aspartic acid, and leucine at the 476th position is replaced with proline (hereinafter abbreviated as "A103P/A264V/Y270D/L476P").

The term "residual enzyme activity after heating" as referred to herein may be referred to as "residual enzymatic activity" or "retention of enzymatic activity" and is a value representing a change in activity before and after an enzyme is subjected to prescribed heating. That is, the residual activity is a value of percentage representing how the activity value after heating has changed as compared with that before heating upon the measurement of enzymatic activity under the same condition. The condition of the term "heating" as referred to herein is a stationary treatment in a buffer solution at 60° C. for one hour, and a ratio of the foregoing enzymatic activity value before and after this heating is represented by percentage.

Also, the term "denaturation temperature $T_m$" as referred to herein is a value determined by the measurement by differential scanning microcalorimetry. A temperature rise rate of an enzyme solution as a preparation in this measure was set up at 60° C. per hour.

The heat-resistant bilirubin oxidase mutant according to an embodiment is able to maintain the enzymatic activity in a prescribed level or more even after heating.

The heat resistant bilirubin oxidase mutant as referred to herein may be referred to as "thermo stable mutant" or "thermo stable BO mutant." After three generations of stability evolution, the $T_m$ value of the thermo-stable mutant increased by 10° C. Furthermore, this mutant almost retained full activity against ferrocyanide of the native enzyme.

In an embodiment, the durability of a biofuel cell using a biocathode including a thermo-stable BO mutant was increased many fold compared with that of the native BO.

Additional features and advantages are described herein, and will be apparent from, the following Detailed Description and the figures.

BRIEF DESCRIPTION OF THE FIGURES

FIG. 5 is a diagram showing decreases of the relative current by a biocathode with native BO and a biocathode with a thermo-stable BO mutant and the relative power density by a biofuel cell using the biocathodes under a long-term preservation at room temperature. Squares show the relative current density and circles show the relative power density, respectively.

DETAILED DESCRIPTION

Figure 1:
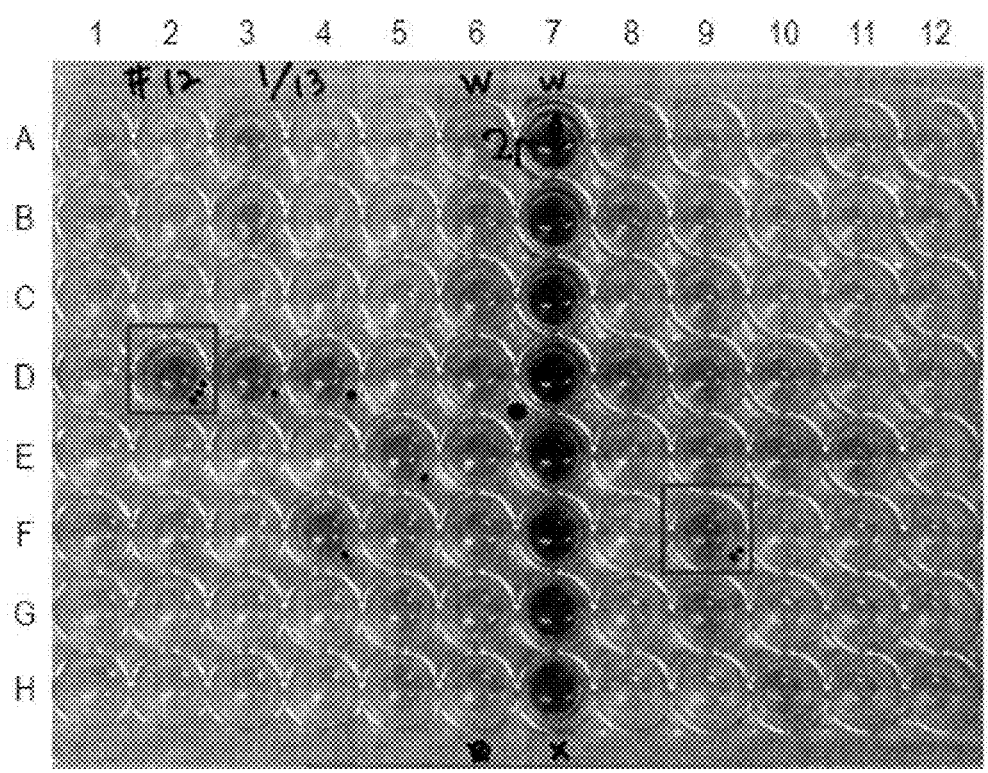
FIG. 1 is a diagram showing one example of thermal stabilization screening and showing the behavior of color generation of ABTS (one hour after the start of the reaction).

The present application is directed to a heat-resistant bilirubin oxidase mutant. The bilirubin oxidase mutant is obtained by deletion, replacement, addition or insertion of at least one amino acid residue of a wild type amino sequence of SEQ. ID. No. 1 of a bilirubin oxidase derived from an imperfect filamentous fungus, *Myrothecium verrucaria*. A biocathode including an immobilized thermo stable bilirubin oxidase mutant and its use in a biofuel cell is disclosed. The present invention will be described in further detail according to an embodiment given below taken in conjunction with the drawings.

Next, specific examples according to an embodiment are described on the basis of the experimental results.

Example 1 cDNA Cloning of BO Derived from *M. verrucaria*

1-1. Culture of *M. verrucaria* and Isolation of Messenger RNA:

A strain of *M. verrucaria* NBRC (IFO) 6113 used in the present Example was purchased from National institute of Technology and Evaluation, Department of Biotechnology. The obtained lyophilizate was suspended in a condensate (polypeptone: 0.5%, yeast extract: 0.3%, $MgSO_4.7H_2O$: 0.1%), and this suspension was inoculated on a potato dextrose agar (PDA) plate (potato dextrose: 2.4%, agarose: 1.5%). As a result of culture at room temperature for 5 to 7 days, the surface of the PDA plate was covered by a white hypha. This was scraped by a spatula and preserved at −80° C. The yield of the bacterial cell was from 50 to 60 mg (wet weight) per PDA plate (diameter: 9 cm).

A messenger RNA (hereinafter referred to a "mRNA") was extracted as a total RNA (a mixture of mRNA, ribosomal RNA and transfer RNA). The total RNA was obtained in an amount of 100 μg (quantitatively determined by UV absorption) from about 100 mg of the lyophilizate powder of *M. verrucaria*, and a ¼ portion thereof was used as a template RNA of one reaction of the next reverse transcription PCR.

1-2. Preparation of BO Gene Fragment by Reverse Transcription PCR:

The reverse transcription PCR was carried out by using a OneStep RT-PCR kit (manufactured by Qiagen Corporation) and using the foregoing total RNA as a template. A PCR primer to be used for the reverse transcription PCR was designed as shown in the following Table 1 on the basis of a previously reported base sequence of cDNA of BO.

TABLE 1

N-Terminus side, HindIII (AAGCTT) site inserted
(SEQ. ID. No. 46)
5'-GGGAAGCTTATGTTCAAACACACACTTGGAGCTG-3'

C-Terminus side, XbaI (TCTAGA) site inserted
(SEQ. ID. No. 47)
5'-GGGTCTAGACTCGTCAGCTGCGGCGTAAGGTCTG-3'

As a result of agarose gel electrophoresis of the resulting PCR product, a strong band could be verified in the vicinity of 1,700 bp. In view of the size of 1,700 bp, this fragment was estimated to be an amplified fragment containing the desired BO gene, and therefore, this fragment was cut out from the agarose gel slab and used in a next step.

1-3. Integration of BO Gene Fragment into pYES2/CT Vector:

The obtained amplified fragment of 1,700 bp was digested by restriction enzymes HindIII and XbaI and then coupled with a pYES2/CT plasmid vector (manufactured by Invitrogen Corporation) as digested by the same enzymes. On that occasion, an alkaline phosphatase derived from Calf intestine (manufactured by Takara Bio Inc.) was used for the dephosphorylation of a 5'-protruding end of the pYES2/CT vector by the restriction enzyme treatment, and T4 DNA ligase (manufactured by Takara Bio Inc.) was used for a coupling reaction between the inserted fragment and the pYES2/CT vector, respectively.

A strain of *E. coli* TOP10 (manufactured by Invitrogen Corporation) was transformed by the thus obtained reaction product and inoculated on an LB/Amp agar plate medium (having a composition as shown in Table 2). After culturing overnight, a colony of a transformant having drug resistance to ampicillin was obtained. This was cultured overnight on 3 mL of an LB/Amp medium, and the plasmid vector was isolated from the resulting bacterial cell.

TABLE 2

| Tryptophan | 1% |
|---|---|
| Yeast extract | 0.5% |
| Sodium chloride | 1% |
| Ampicillin | 0.005% |

As a result of examining the base sequence of the inserted portion containing a BO gene of the resulting plasmid vector, it was found to be SEQ. ID. No. 48.

The base sequence represented in SEQ ID. No. 48 is 1,719 bp and is corresponding to 572 amino acid residues. On the other hand, a BO derived from *M. verrucaria* of a maturation type is constituted of 534 amino acid residues (SEQ. ID. No. 1). The 38 amino acid residues corresponding to a difference therebetween exists on the N-terminus side and are a signal peptide for governing the secretion of a protein existing on the C-terminus side. After translation, the portion is cleaved at the time of secretion.

1-4. Insertion of AAA Sequence:

Next, with respect to the plasmid vector as prepared in 1-3, a part of the base sequence thereof was modified so as to increase the expression amount of the recombinant protein. Concretely, three bases on the upstream side (5'-side) relative to a start codon (ATG) were changed as follows.

TABLE 3

Before modification:
(SEQ. ID. No. 49)
5'- . . . ATTAAG<u>AAA</u>TGTTCAAAC . . . -3'

After modification:
(SEQ. ID. No. 50)
5'- . . . ATTAAG<u>AAAA</u>TGTTCAAAC . . . -3'

The change of these three bases was carried out by a Quick-Change mutagenesis kit (manufactured by Stratagene Corporation) by using a PCR primer as shown in the following Table 4. The detailed experimental procedures followed those in a manual attached to the product.

TABLE 4

N-Terminus side:
(SEQ. ID. No. 51)
5'-CTATAGGGAATATTAAGAAA<u>ATG</u>TTCAAACACACACTTG-3'

C-Terminus side:
(SEQ. ID. No. 52)
5'-CAAGTGTGTGTTTGAA<u>CAT</u>TTTCTTAATATTCCCTATAGTG-3'

The verification of the base sequence was carried out in the entire region of the BO gene including the changed sites. As a result, it was verified that the base sequence was changed as designed. The plasmid vector after changing the sequence is hereinafter referred to as "pYES2/CT-BO vector".

Example 2

Construction of Secretion Expression System of Recombinant BO by *S. cerevisiae*

2-1. Transformation of *S. cerevisiae* by pYES2/CT-BO Vector:

Next, the transformation of *S. cerevisiae* was carried out by using the foregoing pYES2/CT-BO vector. As *S. cerevisiae*, a strain of INVScl (manufactured by Invitrogen Corporation) which is marketed along with the pYES2/CT vector was used. Here, the transformation of *S. cerevisiae* was carried out by a lithium acetate method. With respect to the detailed experimental procedures, a manual attached to the pYES2/CT vector was made by reference. For selecting the transformed yeast, an SCGlu agar plate medium (having a composition as shown in Table 2) was used.

TABLE 5

| | |
|---|---|
| Yeast nitrogen base (YNB) | 0.17% |
| $(NH_4)_2SO_4$ | 0.5% |
| L-Arginine | 0.01% |
| L-Cysteine | 0.01% |
| L-Leucine | 0.01% |
| L-Lysine | 0.01% |
| L-Threonine | 0.01% |
| L-Tryptophan | 0.01% |
| L-Aspartic acid | 0.005% |
| L-Histidine | 0.005% |
| L-Isoleucine | 0.005% |
| L-Methionine | 0.005% |
| L-Phenylalanine | 0.005% |
| L-Proline | 0.005% |
| L-Serine | 0.005% |
| L-Tyrosine | 0.005% |
| L-Valine | 0.005% |
| Adenine | 0.01% |
| D-Glucose | 2% |
| Agarose | 2% |

2-2. Secretion Expression of Recombinant BO:

The colony of the transformant of *S. cerevisiae* by the pYES2/CT-BO vector was inoculated on 15 mL of an SCGlu liquid medium and cultured with shaking at 30° C. for from 14 to 20 hours. The resulting bacterial cell was once precipitated by centrifugation (1,500×g at room temperature for 10 minutes).

Here, after discarding the SCGlu liquid medium, the resulting bacterial cell was added in 50 mL of an SCGal medium (having a composition as shown in Table 6) such that a turbidity ($OD_{600}$) was about 0.5. This was cultured with shaking at 25° C. for from 10 to 14 hours. After the culture, the bacterial cell was removed by centrifugation, the residual culture solution was concentrated to a degree of about 5 mL and dialyzed against a 20 mM sodium phosphate buffer solution (pH: 7.4).

TABLE 6

| | |
|---|---|
| Yeast nitrogen base (YNB) | 0.17% |
| $(NH_4)_2SO_4$ | 0.5% |
| L-Arginine | 0.01% |
| L-Cysteine | 0.01% |
| L-Leucine | 0.01% |
| L-Lysine | 0.01% |
| L-Threonine | 0.01% |
| L-Tryptophan | 0.01% |
| L-Aspartic acid | 0.005% |
| L-Histidine | 0.005% |
| L-Isoleucine | 0.005% |
| L-Methionine | 0.005% |
| L-Phenylalanine | 0.005% |
| L-Proline | 0.005% |
| L-Serine | 0.005% |
| L-Tyrosine | 0.005% |
| L-Valine | 0.005% |
| Adenine | 0.01% |
| D-Galactose | 2% |
| Raffinose | 1% |
| Glycine | 1% |
| $CuSO_4 \cdot 5H_2O$ | 0.003% |

The purification of the recombinant BO was carried out by Ni-NTA affinity chromatography (His-trap HP (1 mL), manufactured by Amersham Biosciences K.K.). The purification method followed that in a manual attached to the product. The recombinant BO obtained after the purification was verified to have a purity of 100 by SDS-PAGE or the like. The yield of the resulting recombinant BO was calculated into 1 L-culture and found to be 0.36 mg.

Example 3

Thermal Stabilization Screening of Recombinant BO by Evolutionary Molecular Engineering Method Next, the recombinant BO was subjected to thermal stabilization screening by an evolutionary molecular engineering method. Concretely, the insertion of random mutation using Error-prone PCR, the preparation of a BO gene library as a transformant, the transformation of *S. cerevisiae* by the BO mutant gene library and the thermal stabilization screening by a 96-well plate were carried out.

3-1. Insertion of Random Mutation Using Error-Prone PCR:

The insertion of random mutation by Error-prone PCR was carried out by using the pYES2/CT-BO vector as a template. The PCR primer on the N-terminus side as used herein was designed so as to contain only one Bg/II side (AGATCT) existing in the downstream of the 218 base pairs relative to the start codon. Also, the C-terminus side was designed in the following manner so as to contain the XbaI site (TCTAGA) (see Table 7).

TABLE 7

N-Terminus side, BglII (AGATCT) site inserted
(SEQ. ID. No. 53)
5'-GTAACCAATCCTGTGAATGGACAAG<u>AGATCT</u>GG-3'

C-Terminus side, XbaI (TCTAGA) site inserted
(SEQ. ID. No. 54)
5'-GGGATAGGCTTACCTTCGAAGGGCCC<u>TCTAGA</u>CTC-3'

The Error-prone PCR was carried out by a GeneMorph PCR mutagenesis kit (manufactured by Stratagene Corporation) by using this primer. With respect to the reaction condition, a manual attached to the same kit was made by reference.

As a result of agarose gel electrophoresis of the resulting PCR product, a PCR fragment of about 1,500 bp could be obtained. The frequency of mutation as calculated from the yield of the resulting PCR product was 1.5 sites per 1,000 bp. With respect to the calculation method, a manual attached to the same kit was made by reference.

3-2. Preparation of BO Gene Library of Mutant:

With respect to the BO gene fragment having mutation randomly inserted thereinto as prepared above in 3-1, integration of the pYES2/CT-BO vector into the BgIII-XbaI sites and transformation of a strain of *E. coli* TOP10 were carried out in the same manner as described above in 1-3. Here, a plasmid library including about 6,600 transformant colonies, namely about 6,600 kinds of transformant genes.

3-3. Transformation of *S. cerevisiae* by Transformant BO Gene Library:

The transformation of a strain of *S. cerevisiae* INVScl (manufactured by Invitrogen Corporation) by the transformant BO gene library was carried out in the same manner as described above in 3-2. A competent cell of *S. cerevisiae* INVScl was prepared by a lithium acetate method. The resulting transformant library was subjected to thermal stabilization screening by using a 96-well plate.

3-4. Thermal Stabilization Screening Experiment Using 96-Well Plate:

A 150-mL portion of an SCGlu medium was poured out into a 96-well plate. One colony of the thus prepared transformant yeast library was inoculated in each well. This was cultured with shaking at 27° C. for from 20 to 23 hours. After this culture, the visual observation revealed that the turbidity of the respective wells became substantially constant.

At this stage, every 96-well plate was once subjected to centrifugation (1,500×g at 20° C. for 10 minutes), thereby once precipitating the bacterial cell. The SCGlu medium was completely removed in such a manner that the bacterial cell precipitated on the bottom of each well was not disturbed. A 180-mL portion of an SCGal medium was poured out thereinto, and the bacterial cell was further cultured with shaking at 27° C. for 8 hours. After this culture, the centrifugation (1,500×g at 20° C. for 10 minutes) was again carried out to precipitate the bacterial cell. 100 mL of this supernatant was transferred into a separate, new 96-well plate. Here, when carrying out heating, a sample solution on this 96-well plate was sealed by a cellophane tape and then allowed to stand in a dry oven at 80° C. for 15 minutes. After heating, the sample solution was rapidly cooled on an ice bath for 5 minutes and then allowed to stand at room temperature for 15 minutes. An equal amount of a 20 mM ABTS solution (100 mM Tris-HCl, pH: 8.0) was mixed therewith. The situation that the solution in the well was colored green with the progress of reaction of ABTS was observed until one hour elapsed after the start of the reaction. Ones exhibiting strong coloration as compared with the wild type as a comparison were picked up, and bacterial cells corresponding thereto were preserved as glycerol stocks at −80° C.

FIG. 1 shows one example of thermal stabilization screening. FIG. 1 shows the behavior of color generation of ABTS one hour after the start of the reaction. All of central two columns (6th and 7th columns from the left side) are concerned with the wild type recombinant BO as a comparison, in which the 6th column is concerned with one having been subjected to heating similar to other wells. The 7th column is concerned with the comparison in the case of the wild type recombinant BO not having been subjected to heating.

It is noted from FIG. 1 that the wells surrounded by a square cause strong color generation as compared with any of the wild types in the 6th column. It is thought that in these wells, a BO mutant having enhanced thermal stability is expressed as compared with the wild type recombinant BO.

In this Example 3, the thermal stabilization screening as described in 3-4 was performed with respect to 4,000 samples in total in 50 sheets of a 96-well plate, and 26 transformant yeasts which are thought to have expressed the heat-resistant BO mutant were chosen.

Plasmid vectors were extracted with the obtained 26 transformant yeasts and subjected to an analysis of base sequence of the BO gene region. As a result, it became clear that the following 26 kinds of mutations were inserted into the BO gene. That is, mutations of the foregoing abbreviations Q49K, Q72E, V81L, Y121S, R147P, A185S, P210L, F225V, G258V, A264V, D322N, N335S, R356L, P359S, D370Y, V371A, P423L, M468V, L476P, V513L, A103P, Y270D, S29.9N, V381L, A418T and R437H were verified.

Example 4

Abundant Expression by Heat-Resistant Mutant *Pichia methanolica*

In the following, in order to achieve abundant expression of the 26 kinds of heat-resistant mutant candidacies discovered by the thermal stabilization screening, the construction of secretion expression system of recombinant BO using a yeast *Pichia methanolica* (hereinafter referred to as "*P. methanolica*") was newly performed, thereby attempting to achieve abundant expression of the wild type and heat-resistant mutant candidacies.

4-1. Preparation of pMETaB-BO Vector and Transformation of *P. methanolica* by this Vector:

First of all, an expression vector to be used in an expression system of *P. methanolica* was prepared. Since a secretion signal: α-factor derived from *S. cerevisiae* is contained in a pMETaB vector (manufactured by Invitrogen Corporation), a gene corresponding to a maturation BO was inserted into its downstream. The amplification of the maturation BO gene region by PCR was carried out by using the pYES2/CT-BO vector as a template and using primers as shown in the following Table 8.

TABLE 8

N-Terminus side, EcoRI (GAATTC) site inserted
(SEQ. ID. No. 55)
5'-GGGAATTCTTGCCCAGATCAGCCCACAGTATC-3'

C-Terminus side, Termination codon, SpeI (ACTAGT) site inserted
(SEQ. ID. No. 56)
5'-GGGACTAGTCACTCGTCAGCTGCGGCGTAAGG-3'

The obtained amplified fragment of 1,500 bp was digested by restriction enzymes EcoRI and SpeI and then coupled with a pMETaB vector as digested by the same enzymes. On the occasion of this coupling reaction, the reaction product was subjected to the same treatment as that described above in 1-3. With respect to the thus prepared BO gene region-containing pMETaB vector (hereinafter referred to as "pMETaB-BO vector"), the verification of the base sequence of the inserted BO gene portion was carried out. In the case of the BO mutant, mutations were inserted into the thus prepared pMETaB-BO vector by QuickChange Mutagenesis Kits (manufactured by Invitrogen Corporation). The subsequent operations were similarly carried out irrespective of the wild type and the mutant.

In addition to the foregoing pMETaB-BO vectors of the wild type and 26 kinds of heat-resistant mutant candidacies, a pMETaB-BO vector of a multiple mutant obtained by combining two, three or four of the 26 kinds of heat-resistant mutant candidacies was similarly prepared and verified with respect to the base sequence.

The transformation of *P. methanolica* by all of the thus prepared pMETaB-BO vectors was carried out. A strain of PMAD11 (manufactured by Invitrogen Corporation) was used as *P. methanolica*. The transformation followed a method described in a manual attached to the pMETaB vector. The selection of the transformed yeast was carried out on an MD agar plate medium (having a composition as shown in Table 9). Competencies of this reaction were all up to 10/1 μg DNA and were substantially coincident with the values described in the manual.

TABLE 9

| | |
|---|---|
| Yeast nitrogen base (YNB) | 1.34% |
| Biotin | 0.00004% |
| D-Glucose | 2% |
| Agarose | 1.5% |

4-2. Abundant Expression of Recombinant BO by *P. methanolica*:

The colony of the transformant yeast on an MD medium as obtained 5 to 7 days after the transformation was cultured overnight on 3 mL of a BMDY medium (having a composition as shown in Table 10). A part of the resulting culture solution was again developed on an MD agar plate medium. A white purified colony obtained 2 to 3 days after this was used for the abundant expression in the next item.

TABLE 10

| | |
|---|---|
| Yeast extract | 1% |
| Peptone | 2% |
| Potassium phosphate buffer solution (pH: 6.0) | 100 mM |
| Yeast nitrogen base (YNB) | 1.34% |
| Biotin | 0.00004% |
| D-Glucose | 2% |

Next, an operation of the abundant expression of recombinant BO by *P. methanolica* was carried out. The purified colony of the transformant yeast was inoculated on 50 mL of a BMDY liquid medium and cultured with shaking at 30° C. overnight. At that time, the $OD_{600}$ was found to be from 2 to 5. The thus obtained bacterial cell was once precipitated by centrifugation (1,500×g at room temperature for 10 minutes), the BMDY liquid medium was removed, and only the bacterial cell was then suspended in 50 to 100 mL of a BMMY liquid medium (having a composition as shown in Table 11). The suspension was cultured with shaking at 27° C. for 24 hours. Thereafter, methanol was added such that a final concentration was 0.5%, and the mixture was further cultured under the same condition for 24 hours. After performing this until elapsing 96 hours, the bacterial cell was removed by centrifugation, and the residual culture solution was concentrated to a degree of about 5 to 10 mL and dialyzed against a 50 mM Tris-HCl buffer (pH: 7.6).

TABLE 11

| | |
|---|---|
| Yeast extract | 1% |
| Peptone | 2% |
| Potassium phosphate buffer solution (pH: 6.0) | 100 mM |
| Yeast nitrogen base (YNB) | 1.34% |

TABLE 11-continued

| | |
|---|---|
| Biotin | 0.00004% |
| Methanol | 0.5% |
| $CuSO_4 \cdot 5H_2O$ | 0.003% |

4-3. Purification of Recombinant BO:

Subsequently, the purification of the recombinant BO by anion-exchange chromatography was carried out. A crude solution containing the recombinant BO as prepared in the preceding step was purified by using an anion-exchange column (HiTrap Q HP, bed volume: 5 mL, manufactured by GE Healthcare Bioscience Corp.). With respect to the purification condition, a previous report (*Biochemistry*, 38, 3034-3042 (1999)) was made by reference.

Next, the purification of the recombinant BO by hydrophobic chromatography was carried out. A column used for the hydrophobic chromatography is a Toyopearl Butyl-650 M column (100 mL, 20 mm×20 cm, manufactured by Tosoh Corporation). With respect to the purification condition, a previous report (Biochemistry, 44, 7004-7012 (2005)) was made by reference. A UV-vis spectrum of the recombinant BO (A246V) obtained after the purification is shown in FIG. 2.

Figure 2:
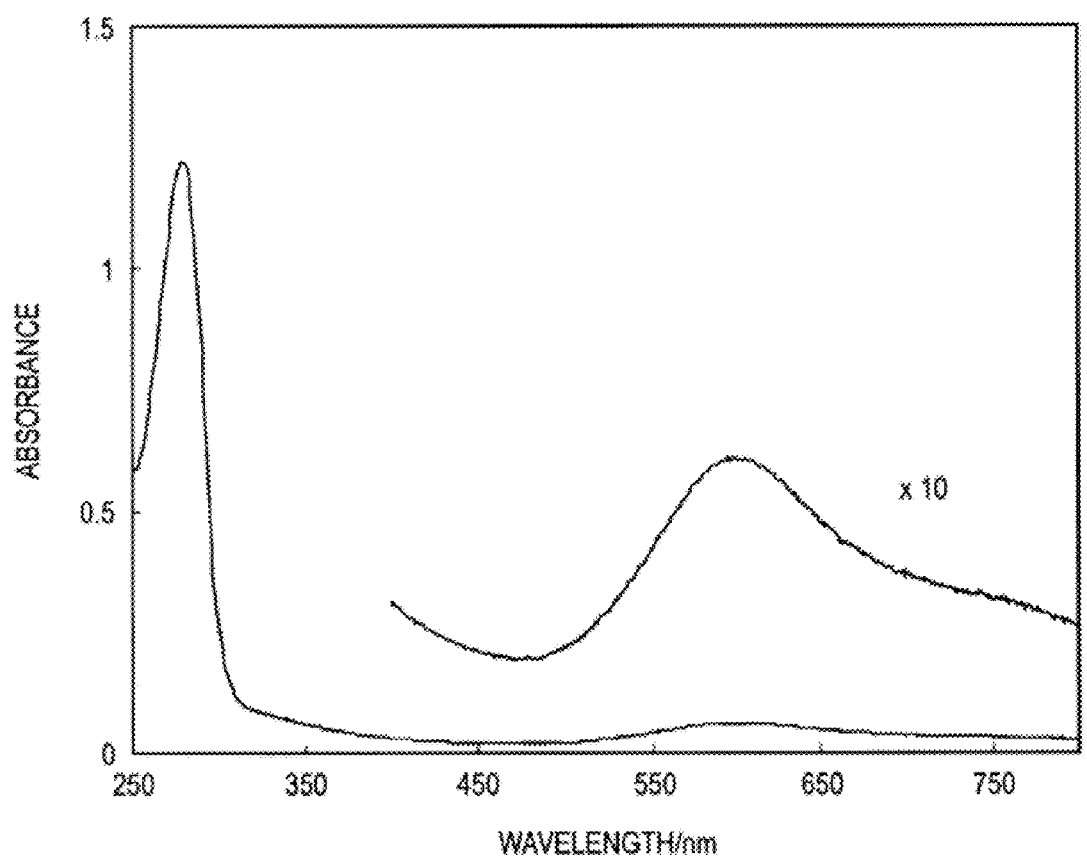
FIG. 2 is a diagram showing a UV-vis spectrum of a recombinant BO mutant.

The spectral pattern of A264V as shown in FIG. 2 was completely coincident with that of a recombinant BO by *P. pastris* in a previous report (*Protein Expression Purif.*, 41, 77-83 (2005)).

A final yield of the abundant culture by *P. methanolica* was 11.7 mg/l L-culture at maximum.

4-4. Evaluation of Heat Resistance:

Next, a recombinant BO by *P. methanolica* and a commercially available BO (manufactured by Amano Enzyme Inc.) were evaluated with respect to the heat resistance. The evaluation of the heat resistance was performed by the comparison in the residual activity after heating. For the measurement of the BO activity, ABTS was used as a substrate, a change in the absorbance at 730 nm with the progress of reaction (derived from an increase of the reaction product of ABTS) was followed. The measurement condition is shown in Table 12. During the activity measurement, the BO concentration was adjusted such that the change in the absorbance at 730 nm was from about 0.01 to 0.2 per minute. The reaction was started by adding an enzyme solution (5 to 20 μL) in an ABTS-containing phosphate buffer solution (2,980 to 2,995 μL).

TABLE 12

| | |
|---|---|
| Buffer solution | 46.5 mM sodium phosphate aqueous solution (pH: 7.0) |
| ABTS concentration | 2 mM (final concentration) |
| $O_2$ concentration | Saturated with air (210 · M, 25° C.) |
| Reaction temperature | 25° C. |

With respect to the 26 kinds in total of the heat-resistant BO mutant candidacies expressed by *P. methanolica* (Q49K, Q72E, V81L, Y121S, R147P, A185S, P210L, F225V, G258V, A264V, D322N, N335S, R356L, P359S, D370Y, V371A, P423L, M468V, L476P, V513L, A103P, Y270D, S299N, V381L, A418T and R437H) and a multiple mutant obtained by combining two, three or four of them, a heat resistance experiment was carried out. With respect to the heating of each enzyme solution, a method of rapidly moving 150 mL of an enzyme solution (100 mM potassium phosphate buffer (pH: 6.0)) as poured out into a 500-mL tube in an ice bath onto a heat block set up at 60° C., allowing it to stand for a fixed time and then rapidly again returning in an ice bath was employed. The results of this heat resistance verification experiment are summarized in Table 13.

4-5. Measurement of Denaturation Temperature:

The denaturation temperature $T_m$ of the 55 kinds of heat-resistant BO mutants having been subjected to evaluation of heat resistance was measured by differential scanning calorimetry (hereinafter referred to as "DSC"). VP-DSC as manufactured by MicroCal, LLC was used for the DSC. An enzyme solution was used in an amount of from 2.0 to 2.5 mg/mL, and the temperature rise was carried out at a rate of 60° C. per hour. The results are summarized along with the heat resistance verification experiment of the activity in Table 13.

TABLE 13

| Residual activity & denaturation temperature | Single mutant | Double mutant | Triple mutant or quartet mutant |
|---|---|---|---|
| 80% or more & 77° C. or higher | | Y121S/L476P, A264V/R356L, A264V/L476P, D322N/M468V | Q49K/V371A/V513L, Y121S/D370Y/L476P, A185S/A264V/L476P, K225V/D322N/M468V, A264V/R356L/L476P, A264V/S299N/L476P, A264V/V381L/L476P, A264V/A418T/L476P, A264V/R437H/L476P, A103P/A264V/Y270D/L476P |
| 50% or more & 75° C. or higher | Q72E, V81L, Y121S, F225V, A264V, D322N, R356L, P359S, D370Y, P423L, M468V, L476P, A103P, S299N, V381L, A418T, R437H | | Q72E/P210L/A264V, V81L/N335S/P423L, F225V/D370Y/L476P |
| 20% or more & 72° C. or higher | Q49K, R147P, A185S, P210L, G258V, N335S, V371A, V513T, V270D | Q49K/V371A, Q72E/P210L, Q72E/A264V, V81L/R147P, V81L/P423L, A185S/G258V, P210L/A264V, F225V/D322N, F225V/L476P, N335S/P423L, R356L/L476P, V371A/V513L | |
| Less than 20% & lower than 72° C. | Wild type, commercial product | | |

The heat-resistant bilirubin oxidase mutant according to the embodiment can be, for example, utilized as a catalyst for realizing an electrochemical four-electron reduction reaction of oxygen in a fuel cell using an electrode having an enzyme immobilized therein, especially on a cathode side of the enzyme cell.

Example 5

Preparation of the Thermo-Stable BO Mutant Used in the Biocathode

The native BO from *Myrothecium verrucaria* was purchased from Amano Enzyme Inc. The thermo-stable BO mutants were obtained by directed evolution with random mutagenesis followed by screening or selection using *Saccharomyces cerevisiae* expression system. Three generations of a stability evolution were done with screening a total of 20,000 clones. The highest thermo-stable mutants obtained were expressed by *Pichia methanolica* system, and its activity and thermo-stability were estimated as follows. BO activity assays in buffer solution were done with ABTS by monitoring the absorption enhancement at 730 nm. For thermo-stability measurements, BO stock solution was incubated at various temperatures between 25 and 90° C. After 10 minutes incubation, a small amount of sample solution was diluted by ~100-fold and the residual activity after the heat treatment was measured at 25° C. The large-scale expression of this thermo-stable BO mutant for the preparation of the biocathode was performed by the high-level expression system using *Penicillium camembertii*.

Example 6

Figure 4:
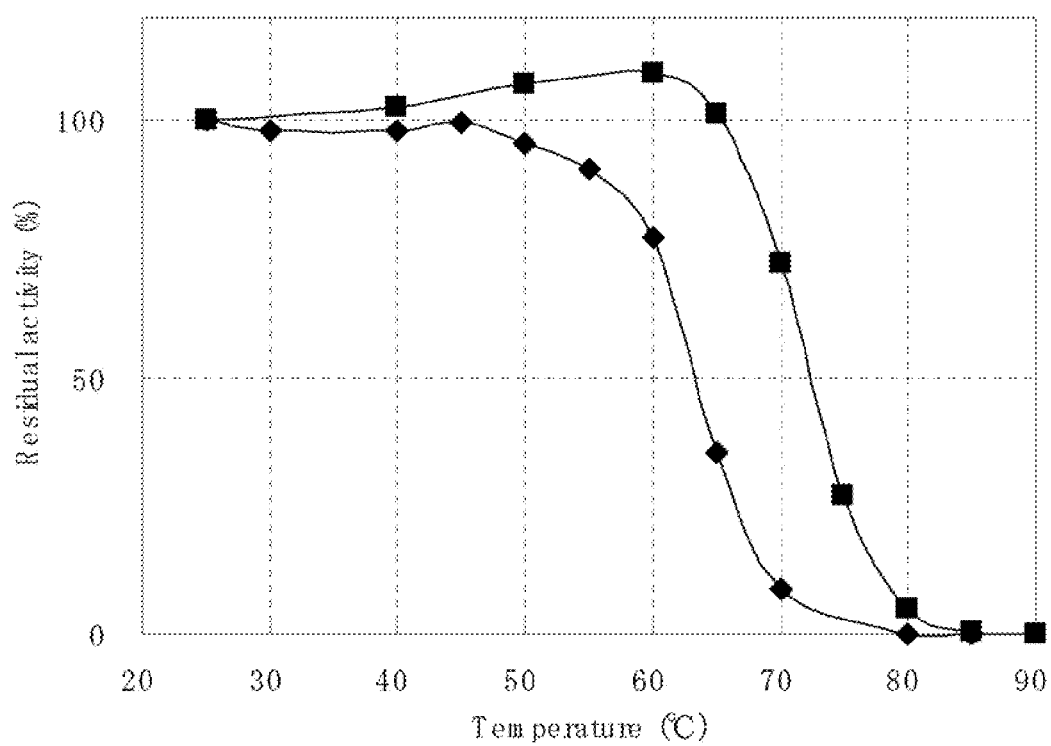
FIG. 4 is a diagram showing thermo-stability of the native BO from Myrothecium verrucaria and its thermostable BO mutant estimated from the residual activity after 10 minutes incubation at various temperatures. Squares show residual activity of thermo stable BO mutant and diamonds show residual activity of native BO, respectively.

Thermo-Stability of the Native BO and its Thermo-Stable Mutant in Buffer Solution The structural gene of the highest thermo-stable BO mutant was sequenced. The sequence revealed that this mutant included 4 amino acid substitutions in 534 amino acids of a mature enzyme. The thermo-stability of native BO from *Myrothecium verrucaria* and the highest thermo-stable BO mutant expressed by *Pichia methanolica*, which is estimated from the residual activity after 10 minutes incubation at various temperatures, is shown in FIG. 4. The inactivation temperature ($T_m$), at which residual activity is 50%, of the native BO from *Myrothecium verrucaria* is 62° C., as shown in FIG. 4. After three generations of stability evolution, the $T_m$ value of the thermo-stable mutant increased by 10° C. Furthermore, this mutant almost retained full activity against ferrocyanide of the native enzyme. From these results, we have been successful in introducing the thermo-stability required for industrial applications without the loss of its activity. However, the $T_m$ value of the thermo-stable BO mutant prepared by large-scale production system using *Penicillium camembertii* decreased by 5° C. as compared with that prepared by *Pichia* host, although the full activity against ferrocyanide was retained. The thermo-stable mutant by *Penicillium camembertii* system, whose $T_m$ value increased by 5° C. as compared to that of native BO, was used in the preparation of the biocathode.

Example 7

Preparation of the Biocathode

Figure 3:
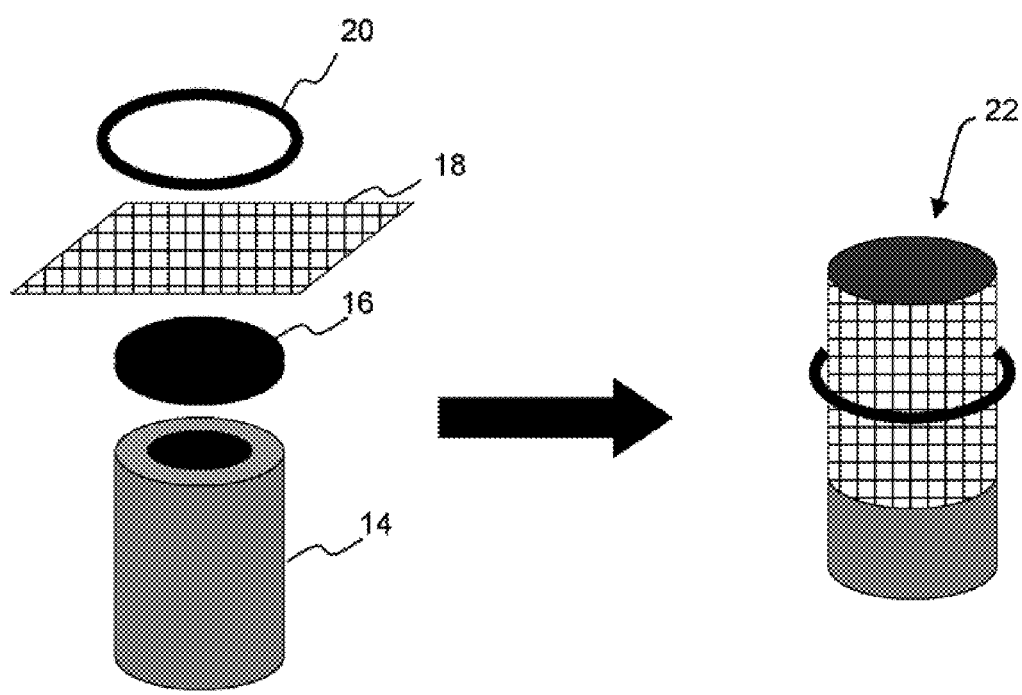
FIG. 3 is a diagram showing immobilization of a CF-biocathode on a rotary disk electrode. The catalytic current by immobilized thermo stable BO mutant on the CF was estimated from cyclic voltammetry.

The obtained thermo-stable BO mutant was immobilized on Carbon-fiber (CF) sheets (BO050, 0.75 mm thickness, Toray Industries Inc., Japan), together with potassium ferricyanide as an electron mediator and poly-L-lysine (Mw: 8,000), as previously reported (Sakai, H. et. al., Energy Environ. Sci. 2009, 2, 133; Sakai et. al., ECS Trans., 2009, 16(38), 9). A glassy carbon disk 14 ("GC disk") for RDE ("rotary disk electrode", a CF-biocathode (6 mm$\phi$) 16, a nylon mesh 18, an O ring 20 are assembled to immobilize the CF-biocathode on a rotary disk electrode 22 as generally illustrated in FIG. 3.

Example 8-1

Evaluation of the Durability of Biocathode

The inactivation of the immobilized thermo stable mutant BO on the biocathode against a long-term preservation under dry condition at room temperature was monitored by measuring its catalytic current of the $O_2$ reduction using cyclic voltammetry (CV). The accurate maximum catalytic current of the $O_2$ reduction on the immobilized BO was observed under the rate-determining condition by the enzyme reaction using a rotary disk electrode technique as generally illustrated in FIG. 3. The electrolyte solutions used in the electrochemical measurement were 50 mM sodium phosphate buffer solution (pH 7.0). A passive-type biofuel cell, in which a non-woven fabric as a separator was sandwiched between bioanode and open-air type biocathode, was constructed as previously reported (Sakai et. al., ECS Trans., 2009, 16(38), 9), and the decrease of the power density against a long-term preservation under dry condition at room temperature was observed. 2.0 M imidazole buffer (pH 7.0) containing 0.4 M glucose was used as the fuel solution to measure the biofuel cells.

Example 8-2

Figure 5:
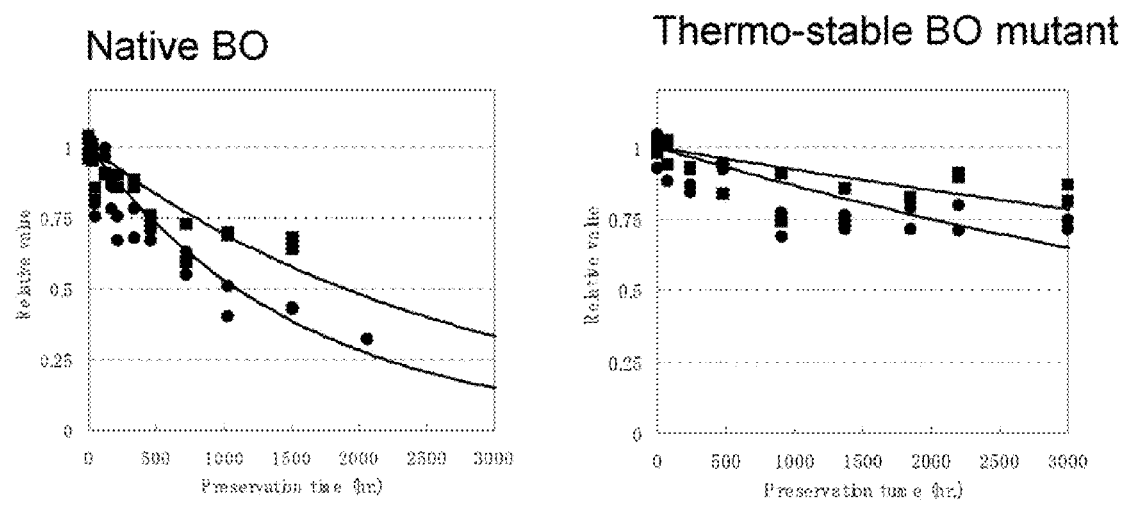

The Durability of the Biocathode with the Native BO and its Thermo-Stable Mutant Under a Long-Term Preservation Decreases of the relative catalytic current and relative power density by the biocathode with the native BO and its thermo-stable mutant during a long-term preservation at room temperature are shown in FIG. 5.

Under dry conditions at room temperature, the biocathode with thermo-stable BO mutant is maintained at more than 80% current density during 4 months (3,000 hour) preservation. The predicted half-life time is more than 2 years, which is more than 20 times long as compared with that of the native BO. Furthermore, the estimated durability of a biofuel cell using a biocathode with thermo-stable BO mutant according to an embodiment, is maintained at more than 80% performance during 4 months preservation under dry condition at room temperature.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

---

The invention is claimed as follows:

1. An isolated heat-resistant bilirubin oxidase mutant protein comprising an amino acid substitution to the amino acid sequence of wild-type bilirubin oxidase protein (SEQ ID NO: 1), wherein the substitution is selected from the group consisting of: Q49K (SEQ ID NO: 2), Q72E (SEQ ID NO: 3), V81L (SEQ ID NO: 4), Y121S (SEQ ID NO: 5), R147P (SEQ ID NO: 6), A185S (SEQ ID NO: 7), P210L (SEQ ID NO: 8), F225V (SEQ ID NO: 9), G258V (SEQ ID NO: 10), A264V (SEQ ID NO: 11), D322N (SEQ ID NO: 12), N335S (SEQ ID NO: 13), R356L (SEQ ID NO: 14), P359S (SEQ ID NO: 15), D370Y (SEQ ID NO: 16), V371A (SEQ ID NO: 17), P423L (SEQ ID NO: 18), M468V (SEQ ID NO: 19), L476P (SEQ ID NO: 20), V513L (SEQ ID NO: 21), A103P (SEQ ID NO: 57), Y270D (SEQ ID NO: 58), S299N (SEQ ID NO: 59), V381L (SEQ ID NO: 60), A418T (SEQ ID NO: 61), R437H (SEQ ID NO: 62), Q49K/V371A (SEQ ID NO: 22), Q72E/P210L (SEQ ID NO: 23), Q72E/A264V (SEQ ID NO: 24), V81L/R147P (SEQ ID NO: 25), V81L/P423L (SEQ ID NO: 26), Y121S/L476P (SEQ ID NO: 27), A185S/G258V (SEQ ID NO: 28), P210L/A264V (SEQ ID NO: 29), F225V/D322N (SEQ ID NO: 30), F225V/L476P (SEQ ID NO: 31), A264V/R356L (SEQ ID NO: 32), A264V/L476P (SEQ ID NO: 33), D322N/M468V (SEQ ID NO: 34), N335S/P423L (SEQ ID NO: 35), R356L/L476P (SEQ ID NO: 36), V371A/V513L (SEQ ID NO: 37), Q49K/V371A/V513L (SEQ ID NO: 38), Q72E/P210L/A264V (SEQ ID NO: 39), V81L/N335S/P423L (SEQ ID NO: 40), Y121S/D370Y/L476P (SEQ ID NO: 41), A185S/A264V/L476P (SEQ ID NO: 42), F225V/D322N/M468V (SEQ ID NO: 43), F225V/D370Y/L476P (SEQ ID NO: 44), A264V/R356L/L476P (SEQ ID NO: 45), A264V/S299N/L476P (SEQ ID NO: 63), A264V/V381L/L476P (SEQ ID NO: 64), A264V/A418T/L476P (SEQ ID NO: 65), A264V/R437H/L476P (SEQ ID NO: 66), and A103P/A264V/Y270D/L476P (SEQ ID NO: 67).

* * * * *